United States Patent
Emanuel

(10) Patent No.: US 10,682,412 B2
(45) Date of Patent: *Jun. 16, 2020

(54) SUSTAINED-RELEASE DRUG CARRIER COMPOSITION

(71) Applicant: POLYPID LTD., Petach-Tikva (IL)

(72) Inventor: Noam Emanuel, Rehovot (IL)

(73) Assignee: POLYPID LTD., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/122,986

(22) Filed: Sep. 6, 2018

(65) Prior Publication Data

US 2019/0070298 A1    Mar. 7, 2019

Related U.S. Application Data

(63) Continuation of application No. 15/244,048, filed on Aug. 23, 2016, now Pat. No. 10,105,443, which is a continuation of application No. 14/523,894, filed on Oct. 26, 2014, now Pat. No. 9,421,271, which is a continuation of application No. 13/003,955, filed as application No. PCT/IL2009/000701 on Jul. 14, 2009, now Pat. No. 8,877,242.

(60) Provisional application No. 61/154,875, filed on Feb. 24, 2009, provisional application No. 61/080,289, filed on Jul. 14, 2008.

(51) Int. Cl.

| | |
|---|---|
| A61K 47/24 | (2006.01) |
| A61L 27/18 | (2006.01) |
| A61L 27/58 | (2006.01) |
| A61K 31/65 | (2006.01) |
| A61K 47/28 | (2006.01) |
| A61K 47/34 | (2017.01) |
| A61K 9/16 | (2006.01) |
| A61L 27/12 | (2006.01) |
| A61L 27/54 | (2006.01) |
| A61L 31/06 | (2006.01) |
| A61L 31/16 | (2006.01) |
| A61K 9/00 | (2006.01) |
| A61K 31/192 | (2006.01) |
| A61K 31/427 | (2006.01) |
| A61K 47/22 | (2006.01) |
| A61K 47/42 | (2017.01) |
| A61K 31/56 | (2006.01) |
| A61L 31/10 | (2006.01) |

(52) U.S. Cl.
CPC ............ *A61K 47/24* (2013.01); *A61K 9/0087* (2013.01); *A61K 31/192* (2013.01); *A61K 31/427* (2013.01); *A61K 31/56* (2013.01); *A61K 31/65* (2013.01); *A61K 47/22* (2013.01); *A61K 47/28* (2013.01); *A61K 47/34* (2013.01); *A61K 47/42* (2013.01); *A61L 27/18* (2013.01); *A61L 27/54* (2013.01); *A61L 27/58* (2013.01); *A61L 31/06* (2013.01); *A61L 31/10* (2013.01); *A61L 31/16* (2013.01); *A61L 2300/204* (2013.01); *A61L 2300/222* (2013.01); *A61L 2300/404* (2013.01); *A61L 2300/406* (2013.01); *A61L 2300/41* (2013.01); *A61L 2300/412* (2013.01); *A61L 2300/602* (2013.01); *A61L 2300/606* (2013.01); *A61L 2300/802* (2013.01); *A61L 2420/04* (2013.01)

(58) Field of Classification Search
CPC ........ A61L 27/12; A61K 47/24; A61K 9/1617
See application file for complete search history.

(56) References Cited

U.S. PATENT DOCUMENTS

| | | |
|---|---|---|
| 3,773,919 A | 11/1973 | Boswell et al. |
| 4,522,863 A | 6/1985 | Lenk et al. |
| 4,578,384 A | 3/1986 | Hollinger |
| 4,882,167 A | 11/1989 | Jang |
| 5,043,166 A | 8/1991 | Barenholz et al. |
| 5,316,771 A | 5/1994 | Barenholz et al. |
| 5,387,221 A | 2/1995 | Bisgaard |
| 5,919,480 A | 7/1999 | Kedar et al. |
| 6,048,551 A | 4/2000 | Hilfinger et al. |
| 6,071,494 A | 6/2000 | Unger et al. |
| 6,083,482 A | 7/2000 | Wang |
| 6,120,805 A | 9/2000 | Spenlehauer et al. |
| 6,156,337 A | 12/2000 | Barenholz et al. |
| 6,162,462 A | 12/2000 | Bolotin et al. |
| 6,238,702 B1 | 5/2001 | Berde et al. |

(Continued)

FOREIGN PATENT DOCUMENTS

| | | |
|---|---|---|
| EP | 2123274 A1 | 11/2009 |
| JP | 61063613 A | 4/1986 |

(Continued)

OTHER PUBLICATIONS

Musumeci, T., et al., PLA/PLGA nanoparticles for sustained release of docetaxel, Int J Pharm. Nov. 15, 2006;325(1-2):172-9. Epub Jun. 23, 2006.*

(Continued)

*Primary Examiner* — H. Sarah Park

(74) *Attorney, Agent, or Firm* — Daniel Feigelson; Fourth Dimension IP

(57) ABSTRACT

The present invention provides compositions for extended release of an active ingredient, comprising a lipid-saturated matrix formed from a biodegradable polymer. The present invention also provides methods of producing the matrix compositions and methods for using the matrix compositions to provide controlled release of an active ingredient in the body of a subject in need thereof.

21 Claims, 13 Drawing Sheets

(56) References Cited

U.S. PATENT DOCUMENTS

| | | |
|---|---|---|
| 6,248,345 B1 | 6/2001 | Goldenheim et al. |
| 6,277,413 B1 | 8/2001 | Sankaram |
| 6,287,587 B2 | 9/2001 | Shegeyuki et al. |
| 6,333,021 B1 | 12/2001 | Schneider et al. |
| 6,403,057 B1 | 6/2002 | Schneider et al. |
| 6,787,132 B1 | 9/2004 | Gabezon et al. |
| 6,793,938 B2 * | 9/2004 | Sankaram ............ A61K 9/1617 424/489 |
| 6,967,028 B2 | 11/2005 | Dulieu et al. |
| 7,045,146 B2 | 5/2006 | Caruso et al. |
| 7,160,554 B2 | 1/2007 | Zalipsky et al. |
| 7,160,557 B2 | 1/2007 | Bernstein |
| 7,749,539 B2 | 7/2010 | Domb |
| 2001/0000470 A1 | 4/2001 | Bernstein et al. |
| 2003/0113379 A1 | 6/2003 | Chen et al. |
| 2003/0161809 A1 | 8/2003 | Houston et al. |
| 2003/0228355 A1 | 12/2003 | Zarif et al. |
| 2004/0018327 A1 | 1/2004 | Wynn et al. |
| 2004/0115240 A1 | 6/2004 | Narhi et al. |
| 2004/0247624 A1 | 12/2004 | Unger et al. |
| 2005/0191344 A1 | 9/2005 | Zalipsky et al. |
| 2005/0208100 A1 | 9/2005 | Weber et al. |
| 2005/0249697 A1 | 11/2005 | Uhrich et al. |
| 2005/0287180 A1 | 12/2005 | Chen |
| 2006/0073203 A1 | 4/2006 | Ljusberg-Wahren et al. |
| 2006/0100370 A1 | 5/2006 | Wellisz et al. |
| 2006/0147520 A1 | 7/2006 | Ruegg |
| 2006/0188573 A1 | 8/2006 | Imberg |
| 2006/0189911 A1 | 8/2006 | Fukuhira et al. |
| 2007/0104656 A1 | 5/2007 | Bernstein |
| 2007/0112438 A1 | 5/2007 | Fukuhira et al. |
| 2007/0141134 A1 | 6/2007 | Kosak |
| 2007/0191963 A1 | 8/2007 | Winterbottom |
| 2007/0280991 A1 | 12/2007 | Glauzer et al. |
| 2008/0085263 A1 | 4/2008 | Thuresson et al. |
| 2008/0095849 A1 | 4/2008 | Wu et al. |
| 2008/0119494 A1 | 5/2008 | Young et al. |
| 2009/0170177 A1 | 7/2009 | Hong et al. |
| 2009/0259302 A1 | 10/2009 | Trollsas et al. |
| 2009/0318355 A1 | 12/2009 | Chen et al. |
| 2009/0324683 A1 * | 12/2009 | Evans ................. A61K 9/0024 424/426 |
| 2010/0196482 A1 | 8/2010 | Radovic-Moreno |
| 2010/0266491 A1 | 10/2010 | Farokhzad et al. |
| 2011/0117184 A1 | 5/2011 | Bromley et al. |

FOREIGN PATENT DOCUMENTS

| | | |
|---|---|---|
| JP | 4046115 A | 1/1992 |
| JP | 4108035 A | 1/1992 |
| WO | 91/07171 A1 | 5/1991 |
| WO | 95/24929 | 9/1995 |
| WO | 96/21470 | 7/1996 |
| WO | 98/07412 A1 | 2/1998 |
| WO | 99/55306 A1 | 11/1999 |
| WO | 99/56731 | 11/1999 |
| WO | 00/03660 A1 | 1/2000 |
| WO | 00/42989 | 7/2000 |
| WO | 00/78357 | 12/2000 |
| WO | 2008/105773 | 9/2008 |
| WO | 2008/124634 | 10/2008 |
| WO | 2009/006311 A2 | 1/2009 |
| WO | 2009/058666 A1 | 5/2009 |
| WO | 2009/061515 A1 | 5/2009 |
| WO | 2009/110939 | 9/2009 |
| WO | 2009/127060 | 10/2009 |
| WO | 2011/037353 A1 | 1/2011 |
| WO | 2011/089595 A1 | 7/2011 |

OTHER PUBLICATIONS

Capito, Remile M. et al., (2008) Self assembly of large and small molecules into hierarchically ordered sacs and membranes. Science 319:1812-1816.

Evora, Carmen et al., (1998) Relating the phagocytosis of microparticles by alveolar macrophages to surface chemistry: The effect cf 1,2-dipalmitoylphosphatidylchoiine. Journai of Controlled Release 51: 143-152.

Heyes, James et al., (2005) Cationic lipid saturation influences intracellular delivery of encapsulated nucleic acids. Journal of Controlled Release 107:276-287.

Lu, James et al., (2009) A Novei mechanism is involved in Cationic Lipid-Mediated Functional siRNA Delivery. Mol Pharm 6(3):763-771.

Juni, Kazuhiko et al., (1985) Moclificaiion of the release rate of aclarubicin from polylactic acid microspheres by using additives. Chem. Pharm Bull (Tokyo) 33(4):1734-1738.

Khoshnoodi, Jamshid et al. (2006) Molecular recognition in the assembly of collagens: terminal ncncollagenous domains are key recognition modules in formation of triple helical protomers. J Biol Chem. 281(50):38117-38121.

Martino, Sabala et al., (2009) Efficient siRNA Delivery by the Cationic Liposome DOTAP in Human Hematopoietic Stem Cells Differentiating into Dendritic Cells. Journal of Biomedicine and Biotechnology, vol. 2009, Article ID 410260, 7 pages.

Moseson, M. W. (2005) Fibrinogen and fibrin structure and functions. J Thromb. Haemost. 3:1894-1904.

Valenick, Leyla V. et al., (2005) Fibronectin fragmentation promotes alpha4beta1 integrin-mediated contraction of a fibrin-fibronectin provisional matrix. Exp. Cell Res 309:48-55.

International Search Report and Written Opinion of PCT/IL09/00701: dated Nov. 12, 2009, 9 pages.

International Search Report and Written Opinion of PCT/IL10/00563 dated Oct. 29, 2019, 7 pages.

International search Report of PCT/IL11/00054 dated Aug. 25, 2011 4 pages.

* cited by examiner

SUSTAINED-RELEASE DRUG CARRIER COMPOSITION

RELATED CASES

This application is a continuation of U.S. Ser. No. 15/244,048, which is a continuation of U.S. Ser. No. 14/523,894, now U.S. Pat. No. 9,421,271, which is a continuation of U.S. Ser. No. 13/003,955, which was filed as a national phase application of PCT/IL2009/000701, filed Jul. 14, 2009, and claims the benefit of U.S. Ser. No. 60/080,289 filed on Jul. 14, 2008 and U.S. Ser. No. 61/154,875 filed on Feb. 24, 2009. The contents of these applications are incorporated herein by reference.

FIELD OF THE INVENTION

The present invention provides compositions for extended release of an active ingredient, comprising a lipid-based matrix with a biodegradable polymer. The present invention also provides methods of producing the matrix compositions and methods for using the matrix compositions to provide controlled release of an active ingredient in the body of a subject in need thereof.

BACKGROUND OF THE INVENTION

Lipid based drug delivery systems are well known in the art of pharmaceutical science. Typically they are used to formulate drugs having poor bioavailability or high toxicity or both. Among the prevalent dosage forms that have gained acceptance are many different types of liposomes, including small unilamellar vesicles, multilamellar vesicles and many other types of liposomes; different types of emulsions, including water in oil emulsions, oil in water emulsions, water-in-oil-in-water double emulsions, submicron emulsions, microemulsions; micelles and many other hydrophobic drug carriers. These types of lipid based delivery systems can be highly specialized to permit targeted drug delivery or decreased toxicity or increased metabolic stability and the like. Extended release in the range of days, weeks and more are not profiles commonly associated with lipid based drug delivery systems in vivo.

Ideally sustained release drug delivery systems should exhibit kinetic and other characteristics readily controlled by the types and ratios of the specific excipients used. Advantageously the sustained release drug delivery systems should provide solutions for hydrophilic, amphipathic as well as hydrophobic drugs.

Periodontitis

The use of systemic doxycycline and NSAIDs in combination therapy has been shown to suppress tissue damage in the gingiva of chronic periodontitis patients. Tissue damage is caused by the action of pathogenic bacteria in combination with host matrix metalloproteinase (MMP) activity. Antibiotic treatment in combination with anti-inflammatory medication suppresses these two pathways. An increase in efficacy and reduction of side effects of treatment would be achieved by a means of releasing these medications locally in a controlled fashion.

Bone Augmentation

Bone diseases requiring bone augmentation include benign and malignant bone tumors, cancers situated in bones, infectious bone diseases, and other bone diseases of etiology related to endocrinology, autoimmunity, poor nutrition, genetic factors, and an imbalance between bone growth and resorption. Examples are diseases such as osteosarcoma/malignant fibrous histiocytoma of bone (PDQ), osteosarcoma, chondrosarcoma, Ewing's sarcoma, malignant fibrous histiocytoma, fibrosarcoma and malignant fibrous histiocytoma, giant cell tumor of bone, chordoma, lymphoma, multiple myeloma, osteoarthritis, Paget's disease of bone, arthritis, degenerative changes, osteoporosis, osteogenesis imperfecta, bone spurs, renal osteodystrophy, hyperparathyroidism, osteomyelitis, enchondroma, osteochondroma, osteopetrosis, bone and joint problems associated with diabetes.

Immediate and delayed infection is a major complication in the field of orthopedics. Reducing the complications after orthopedic treatment will induce the efficiency and success of the orthopedic treatment and in some cases it will reduce the mortality. There is also a need to allow treatment in infected sites and to induce the efficacy of the treatment in the infected sites.

Another important aspect in the field of orthopedics or orthopedic surgery is the need to accelerate soft and hard tissue recovery in reparative and regenerative procedures.

Liposomes and Biodegradable Polymers in Drug Delivery

To date the use of lipids in conjunction with biopolymers has been contemplated but these have not yet been introduced successfully into clinical practice.

U.S. Pat. No. 3,773,919 to Boswell et al describes the use of polymers derived from alpha-hydroxycarboxylic acids, including lactic acid, glycolic acid, and copolymers thereof, and their use in sustained release formulations. Such polymer exhibit slow biodegradability but typically have limited drug-holding capacity.

Liposomes are described in U.S. Pat. No. 4,522,803 to Lenk et al. Liposomes typically exhibit adequate drug delivery drug-holding capacity but relatively limited in vivo half-lives. Many different types of liposomes have been developed for particular applications. Examples can be found in U.S. Pat. Nos. 5,043,166; 5,316,771; 5,919,480; 6,156,337; 6,162,462; 6,787,132; 7,160,554, among others.

U.S. Pat. Nos. 6,333,021 and 6,403,057 to Schneider et al disclose microcapsules having a biodegradable membrane encapsulating a gas core. The membrane, comprising water insoluble lipids with up to 75% by weight of biodegradable polymers, encapsulating a core filled with air or a gas. The microcapsules may be non-coalescent, dry and instantly dispersible, and useful as delivery vehicles for therapeutically active agents and/or as contrast agents for imaging of body organs. The microcapsules are produced by a method in which a water-in-oil emulsion is made from an organic solution comprising a dissolved lipid and an aqueous solution containing a surfactant. The freeze-dried mixture is re-dispersed in an aqueous carrier, and the microcapsules are dried. The presence of water throughout the process precludes formation of a water-resistant, lipid-saturated matrix; thus, these materials are subject to bulk-type degradation in vivo.

U.S. Pat. Nos. 6,277,413 and 6,793,938 to Sankaram disclose biodegradable lipid/polymer-containing compositions, formed by the following process: a) forming a water-in-oil emulsion from a first aqueous phase and a volatile organic solvent phase comprising a volatile organic solvent, a biodegradable polymer or copolymer that is soluble in organic solvent, and a lipid; b) dispersing the "water-in-oil" emulsion into a surfactant-free second aqueous phase to form solvent spherules, and c) removing the volatile organic solvent from the solvent spherules to form a microsphere composition suspended in the second aqueous phase. The methods disclosed utilize aqueous solutions, precluding formation of a water-resistant, lipid-saturated matrix.

U.S. Pat. No. 4,882,167 to Jang discloses a controlled release matrix for tablets or implants of biologically active agents produced by dry direct compression of a hydrophobic carbohydrate polymer, e.g. ethyl cellulose; and a difficult-to-digest soluble component, i.e. a wax, e.g. carnauba wax, a fatty acid material, or a neutral lipid. The carbohydrate polymers utilized, are unsuitable for release on a scale of weeks or months following administration by injection or implantation. In addition, the compositions are produced without any solvents (aqueous or organic), precluding formation of the homogenous lipid-saturated matrix structures.

US patent application 2006/0189911 to Fukuhira et al discloses an anti-adhesion membrane of a honeycomb film made of polylactic acid as a biodegradable polymer and a phospholipid. No disclosure is provided for modification of the membrane for use as a delivery system, e.g. for antibiotics or NSAID drugs. In addition, the disclosed membranes are required to be cast under conditions of high humidity, thus precluding formation of a water-resistant, lipid-saturated matrix; these implants are accordingly subject to bulk-type degradation in vivo.

US patent application 2006/0073203 to Ljusberg-Wahren et al discloses an orally administrable composition comprising a dry mixture of polymer, lipid and bioactive agent, intended upon contact with water or gastrointestinal fluids to form particles comprising the lipid, the bioactive agent, and optionally also water. The polymers utilized, disintegrate in the digestive tract during the digestive process; e.g. a time period of less than one day. Such compositions are completely unsuitable for release on a scale of weeks or months following administration by injection or implantation.

None of the prior art provides compositions adapted to achieve sustained release or programmed release or controlled release from a lipid-saturated polymeric matrix for periodontal or orthopedic uses. None of the above references demonstrates use of the disclosed compositions in delivery of an NSAID compound, an antibiotic compound, or a compound useful for bone augmentation.

SUMMARY OF THE INVENTION

The present invention provides compositions for extended release of an active ingredient, comprising a lipid-based matrix comprising a biodegradable polymer. The present invention also provides methods of producing the matrix compositions and methods for using the matrix compositions to provide controlled release of an active ingredient in the body of a subject in need thereof.

In one aspect, the present invention provides a matrix composition comprising: (a) a biodegradable pharmaceutically acceptable polymer in association with a first lipid having a polar group; (b) a second lipid selected from phospholipids having hydrocarbon chains of at least 14 carbons; and (c) a pharmaceutical active agent, where the matrix composition is adapted for providing sustained release of the pharmaceutical agent. In specific embodiments, the polymer and the phospholipids form a matrix composition that is substantially free of water.

According to particular embodiments the biodegradable polymer comprises a polyester selected from the group consisting of PLA (polylactic acid), PGA (poly glycolic acid), PLGA (poly (lactic-co-glycolic acid)) and combinations thereof.

According to particular embodiments the first lipid having a polar group is selected from a sterol, a tocopherol and a phosphatidylethanolamine. According to particular embodiments the first lipid is mixed with the biodegradable polymer to form a non-covalent association.

According to some embodiments the second lipid comprises a phosphatidylcholine. According to some embodiments the second lipid comprises a mixture of phosphatidylcholines. According to some embodiments the second lipid comprises a mixture of a phosphatidylcholine and a phosphatidylethanolamine, or any other types of phospholipids.

Any type of drug molecule may be incorporated into the matrix compositions for sustained and/or controlled release. According to particular embodiments the pharmaceutically active agent is selected from the group consisting of an antibiotic, an antifungal, an NSAID, a steroid, an anti-cancer agent, an osteogenic factor and a bone resorption inhibitor. According to alternative embodiments the pharmaceutical active agent is selected from a hydrophobic agent, an amphipathic agent or a water soluble agent. Each possibility represents a separate embodiment of the present invention.

In another embodiment, the phospholipid is a phosphatidylcholine having fatty acid moieties of at least 14 carbons. In another embodiment, the composition further comprises a phosphatidylethanolamine having fatty acid moieties of at least 14 carbons. In another embodiment, the composition further comprises cholesterol. In another embodiment, the matrix composition is homogeneous. In another embodiment, the matrix composition is in the form of a lipid-based matrix whose shape and boundaries are determined by the biodegradable polymer. In another embodiment, the matrix composition is in the form of an implant.

In some embodiments, the pharmaceutical active agent is an antibiotic incorporated into the matrix composition. In some embodiments, the antibiotic has low water solubility. In another embodiment, the antibiotic is a hydrophobic antibiotic. In another embodiment, the antibiotic is an amphipathic antibiotic. In another embodiment, the composition further comprises a non-steroidal anti-inflammatory drug (NSAID). In another embodiment, the NSAID as well is incorporated into the matrix composition. In another embodiment, the NSAID has low water solubility. Each possibility represents a separate embodiment of the present invention.

In a particular embodiment, the present invention provides a matrix composition comprising: (a) biodegradable polyester; (b) a sterol; (c) a phosphatidylethanolamine having fatty acid moieties of at least 14 carbons; (d) a phosphatidylcholine having fatty acid moieties of at least 14 carbons; and (e) an antibiotic or antifungal agent. In another embodiment, the matrix composition comprises at least 50% lipid by weight. In another embodiment, the matrix composition is homogeneous. In another embodiment, the matrix composition is in the form of a lipid-based matrix whose shape and boundaries are determined by the biodegradable polymer. In another embodiment, the matrix composition is in the form of an implant.

According to alternative embodiments the antibiotic or antifungal agent is selected from a hydrophobic agent, an amphipathic agent or a water soluble agent. Each possibility represents a separate embodiment of the present invention.

In another embodiment, the present invention provides a matrix composition comprising: (a) biodegradable polyester; (b) a sterol, (c) a phosphatidylethanolamine having fatty acid moieties of at least 14 carbons; (d) a phosphatidylcholine having fatty acid moieties of at least 14 carbons; and (e) a non-steroidal anti-inflammatory drug (NSAID). In another embodiment, the matrix composition comprises at least 50% lipid. In another embodiment, the NSAID has low water solubility. In another embodiment, the NSAID is a hydrophobic NSAID. In another embodiment, the NSAID is an amphipathic NSAID. In another embodiment, the matrix composition is in the form of a lipid-based matrix whose shape and boundaries are determined by the biodegradable polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) biodegradable polyester; (b) a sterol; (c) a phosphatidylethanolamine having fatty acid moieties of at least 14 carbons, (d) a phosphatidylcholine having fatty acid moieties of at least 14 carbons; and (e) an osteogenic factor or a bone resorption inhibitor. In another embodiment, the matrix composition comprises at least 50% lipid. In another embodiment, the bone resorption inhibitor has low water solubility. In another embodiment, the bone resorption inhibitor is a hydrophobic bone resorption inhibitor. In another embodiment, the bone resorption inhibitor is an amphipathic bone resorption inhibitor. In another embodiment, the composition further comprises an NSAID. In another embodiment, the NSAID as well is incorporated into the matrix composition. In another embodiment, the matrix composition is in the form of a lipid-based matrix whose shape and boundaries are determined by the biodegradable polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) biodegradable polyester; (b) a sterol; (c) a phosphatidylethanolamine having saturated fatty acid moieties of at least 14 carbons; (d) a phosphatidylcholine having saturated fatty acid moieties of at least 14 carbons; (e) an active agent; and (f) a targeting moiety capable of interacting with a surface molecule of a target cell. In another embodiment, the active agent is selected from the group consisting of an NSAID, an antibiotic, an antifungal agent, a steroid, an anti-cancer agent, an osteogenic factor and a bone resorption inhibitor. In another embodiment, the polymer and the phospholipid form a matrix composition that is substantially free of water. In another embodiment, the matrix composition is capable of being degraded in vivo to vesicles into which some or all the mass of the released active agent is integrated. In another embodiment, the matrix composition is capable of being degraded in vivo to form vesicles into which the active agent and the targeting moiety are integrated. Each possibility represents a separate embodiment of the present invention.

In another embodiment, the present invention provides a pharmaceutical composition comprising a matrix composition of the present invention and a pharmaceutically acceptable excipient. In another embodiment, the matrix composition is in the form of microspheres. In another embodiment, the present invention provides a pharmaceutical composition comprising microspheres of the present invention and a pharmaceutically acceptable excipient. In another embodiment, the pharmaceutical composition is in a parenterally injectable form. In another embodiment, the pharmaceutical composition is in an infusible form. In another embodiment, the excipient is compatible for injection. In another embodiment, the excipient is compatible for infusion. Each possibility represents a separate embodiment of the present invention.

In another embodiment, a matrix composition of the present invention is in the form of an implant, following evaporation of the organic solvents. In another embodiment, the implant is homogeneous. Each possibility represents a separate embodiment of the present invention.

In some embodiments, the biodegradable polyester of the present invention is associated with the sterol via non-covalent bonds. In some embodiments, the biodegradable polyester of the present invention is associated with the sterol via hydrogen bonds.

In another embodiment, the process of creating an implant from a composition of the present invention comprises the steps of (a) creating a matrix composition according to a method of the present invention in the form of a bulk material, and (b) transferring the bulk material into a mold or solid receptacle of a desired shaped.

Also provided herein are methods for making the compositions of the invention and methods of use thereof.

According to another aspect a matrix composition for sustained release of a pharmaceutical agent is generated by a process comprising: providing a first solution or dispersion of a volatile organic solvent comprising a biodegradable polymer and a first lipid having a polar group; providing a second solution or dispersion comprising a second volatile organic solvent and a second lipid, the second lipid comprising at least one phospholipid, and a pharmaceutical active agent; mixing the first and second solutions to form a homogeneous mixture; evaporating the volatile solvents to produce a homogeneous polymer phospholipid matrix comprising a pharmaceutical active agent. The selection of the specific solvents is made according to the specific drug and other substances used in the particular formulation intended to entrap a specific active and to release it in a specific pre-planned rate and duration. The evaporation is conducted at controlled temperature determined according to the properties of the solution obtained.

According to the present disclosure the use of different types of volatile organic solutions, and the absence of water throughout the process, enable the formation of homogeneous water-resistant, lipid based matrix compositions. According to various embodiments the first and second solvents can be the same or different. According to some embodiments one solvent can be non-polar and the other preferably water-miscible.

In another embodiment, the matrix composition of methods and compositions of the present invention is substantially free of water. "Substantially free of water" refers, in another embodiment, to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water, as described herein, enables lipid saturation. Lipid saturation confers upon the matrix composition ability to resist bulk degradation in vivo; thus, the matrix composition exhibits the ability to mediate extended release on a scale of several days, weeks or months.

In another embodiment, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

In another embodiment, the present invention provides a method of producing a matrix composition, the method comprising the steps of (a) combining with a non-polar, volatile organic solvent: (i) a biodegradable polyester and (ii) a sterol; (b) combining with a water-miscible, volatile organic solvent: (i) an active agent selected from the group consisting of a non-steroidal anti-inflammatory drug (NSAID), an antibiotic, an antifungal a steroid, an anti-cancer agent, and osteogenic factor and a bone resorption inhibitor; (ii) a phosphatidylethanolamine; and (iii) a phosphatidylcholine; and (c) mixing and homogenizing the products resulting from steps (a) and (b). In another embodiment, the phosphatidylethanolamine is included in the non-polar, volatile organic solvent instead of the water-miscible, volatile organic solvent. In another embodiment, the biodegradable polyester is selected from the group consisting of PLA, PGA and PLGA. In another embodiment, the biodegradable polymer is any other suitable biodegradable polyester known in the art. In another embodiment, the mixture containing the non-polar, organic solvent is homogenized prior to mixing it with the mixture organic solvent. In another embodiment, the mixture containing the water-miscible, organic solvent is homogenized prior to mixing it with the mixture containing the non-polar, organic solvent. In another embodiment, the polymer in the mixture of step (a) is lipid saturated. In another embodiment, the matrix composition is lipid saturated. Each possibility represents a separate embodiment of the present invention.

In another embodiment, the matrix composition of the present invention can be used for coating fully or partially the surface of different substrates. In another embodiment substrates to be coated include at least one material selected from the group consisting of carbon fibers, stainless steel, cobalt-chromium, titanium alloy, tantalum, ceramic and collagen or gelatin. In another embodiment substrates may include any medical devices such as orthopedic nails, orthopedic screws, orthopedic staples, orthopedic wires and orthopedic pins used in orthopedic surgery, metal or polymeric implants used in both orthopedic and periodontal surgery, bone filler particles and absorbable gelatin sponge. Bone filler particles can be any one of allogeneic (i.e., from human sources), xenogeneic (i.e., from animal sources) and artificial bone particles. In another embodiment a treatment using the coated substrates and administration of the coated substrates will follow procedures known in the art for treatment and administration of similar uncoated substrates. In another embodiment bone filler particles coated with the biodegradable matrix of the present invention are administered substantially as a single ingredient (not administered as part of a mixture with other ingredients). Alternatively, the coated bone filler particles are mixed with any other commercially available bone filler particles or autologous bone before administration. In another embodiment, the mixture of bone filler particles comprises at least one of: non-coated particles, particles coated with matrix compositions incorporating a pharmaceutically active agent, particles coated with matrix compositions incorporating a plurality of pharmaceutically active agents or a combination thereof. In another embodiment the amounts, ratios and types of ingredients forming the matrix composition of the present invention are varied so to adjust the polymer-lipid basis to the biophysical/biochemical properties of the pharmaceutically active agent, the therapeutically effective dose of the pharmaceutically active agent and to the desired sustained release time period (typically in the range of days to months).

It is to be emphasized that the sustained release period using the compositions of the present invention can be programmed taking into account two major factors: (i) the weight ratio between the polymer and the lipid content, specifically the phospholipid having fatty acid moieties of at least 14 carbons, and (ii) the biochemical and/or biophysical properties of the biopolymer and the lipid. Specifically, the degradation rate of the polymer and the fluidity of the lipid should be considered. For example, a PLGA (85:15) polymer will degrade slower than a PLGA (50:50) polymer. A phosphatidylcholine (14:0) is more fluid (less rigid and less ordered) at body temperature than a phosphatidylcholine (18:0). Thus, for example, the release rate of a drug incorporated in a matrix composition comprising PLGA (85:15) and phosphatidylcholine (18:0) will be slower than that of a drug incorporated in a matrix composed of PLGA (50:50) and phosphatidylcholine (14:0). Another aspect that will determine the release rate is the physical characteristics of the entrapped or impregnated drug. In addition, the release rate of drugs can further be controlled by the addition of other lipids into the formulation of the second solution. This can includes fatty acids of different length such as lauric acid (C12:0), membrane active sterols (such as cholesterol) or other phospholipids such as phosphatidylethanolamine. According to various embodiments the active agent is released from the composition over a desired period ranging between several days to several months.

These and other features and advantages of the present invention will become more readily understood and appreciated from the detailed description of the invention that follows.

DETAILED DESCRIPTION OF THE INVENTION

Figure 1A:
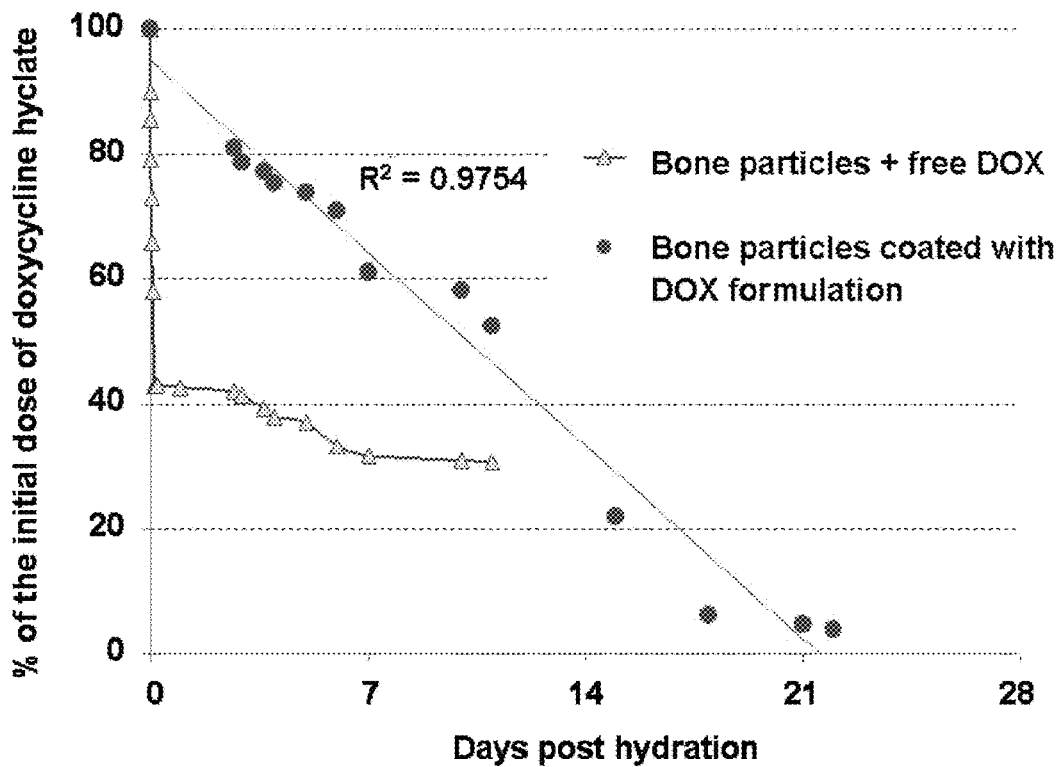
FIGS. 1A and 1B: Doxycycline hyclate (DOX) encapsulated in the formulation of the present invention is being released constantly for at least 3 weeks. A) DOX released from a matrix comprising PLGA 85:15, cholesterol, alpha-tocopherol, and DSPC (18:0); B) DOX released from a matrix comprising PLGA 85:15, cholesterol, and DSPC (18:0).

The present invention provides compositions for extended release of an active ingredient, comprising a lipid-based matrix comprising a biodegradable polymer. The present invention also provides methods of producing the matrix compositions and methods for using the matrix compositions to provide controlled release of an active ingredient in the body of a subject in need thereof.

The term "controlled release" refers to control of the rate and/or quantity of pharmaceutically active agent(s) delivered by the matrix compositions of the invention. The controlled release can be continuous or discontinuous, and/or linear or non-linear.

The term "sustained release" means that pharmaceutical active agent is released over an extended period of time.

In certain embodiments, the present invention provides a matrix composition comprising: (a) biodegradable polyester; (b) a phosphoglyceride having hydrocarbon moieties of at least 14 carbons; and (c) a pharmaceutical active agent. According to some embodiments the pharmaceutical agent is selected from the group consisting of an antibiotic, an antifungal, an NSAID, a steroid, an anticancer agent, an osteogenic factor and a bone resorption inhibitor.

In certain embodiments the phosphoglyceride is a phospholipid. In some embodiments, the phospholipid is a phosphatidylcholine having fatty acid moieties of at least 14 carbons. In another embodiment, the composition further comprises a phosphatidylethanolamine having a fatty acid moieties of at least 14 carbons. In another embodiment, the composition further comprises a sterol. In some embodiments the sterol is cholesterol.

In another embodiment, the matrix composition is lipid saturated. "Lipid saturated," as used herein, refers to saturation of the polymer of the matrix composition with lipids including phospholipids, in combination with any hydrophobic drug and targeting moiety present in the matrix, and any other lipids that may be present. The matrix composition is saturated by whatever lipids are present. Lipid-saturated matrices of the present invention exhibit the additional advantage of not requiring a synthetic emulsifier or surfactant such as polyvinyl alcohol; thus, compositions of the present invention are typically substantially free of polyvinyl alcohol. Methods for determining the polymer:lipid ratio to attain lipid saturation and methods of determining the degree of lipid saturation of a matrix are described hereinbelow.

In another embodiment, the matrix composition is homogeneous. In another embodiment, the matrix composition is in the form of a lipid-saturated matrix whose shape and boundaries are determined by the biodegradable polymer. In another embodiment, the matrix composition is in the form of an implant. Preferably, the polyester, the phosphatidylethanolamine, and the sterol are incorporated into the matrix composition. In another embodiment, the phosphatidylcholine is also incorporated into the matrix composition. In another embodiment, the antibiotic is also incorporated into the matrix composition. In another embodiment, the antibiotic has low water solubility. In another embodiment, the antibiotic is a hydrophobic antibiotic. In another embodiment, the antibiotic is an amphipathic antibiotic. In another embodiment, the composition further comprises a non-steroidal anti-inflammatory drug (NSAID). In another embodiment, the NSAID as well is incorporated into the matrix composition. In another embodiment, the NSAID has low water solubility. Each possibility represents a separate embodiment of the present invention.

In one embodiment, the present invention provides a matrix composition comprising: (a) biodegradable polyester; (b) a sterol; (c) a phosphatidylethanolamine having a fatty acid moieties of at least 14 carbons; (d) a phosphatidylcholine having a fatty acid moieties of at least 14 carbons; and (e) an antibiotic or an antifungal. In another embodiment, the matrix composition is lipid saturated. Preferably, the polyester, the phosphatidylethanolamine, and the sterol are incorporated into the matrix composition. In another embodiment, the phosphatidylcholine is also incorporated into the matrix composition. In another embodiment, the antibiotic is also incorporated into the matrix composition. In another embodiment, the antibiotic has low water solubility. In another embodiment, the antibiotic is a hydrophobic antibiotic. In another embodiment, the antibiotic is an amphipathic antibiotic. In another embodiment, the composition further comprises a non-steroidal anti-inflammatory drug (NSAID). In another embodiment, the NSAID as well is incorporated into the matrix composition. In another embodiment, the NSAID has low water solubility. In another embodiment, the matrix composition is in the form of a lipid-saturated matrix whose shape and boundaries are influenced by the nature of the biodegradable polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) biodegradable polyester; (b) a sterol, (c) a phosphatidylethanolamine having fatty acid moieties of at least 14 carbons, (d) a phosphatidylcholine having fatty acid moieties of at least 14 carbons, (e) a non-steroidal anti-inflammatory drug (NSAID). In another embodiment, the matrix composition is lipid saturated. Preferably, the polyester, the phosphatidylethanolamine, and the sterol are incorporated into the matrix composition. In another embodiment, the phosphatidylcholine is also incorporated into the matrix composition. In another embodiment, the NSAID is also incorporated into the matrix composition. In another embodiment, the NSAID has low water solubility. In another embodiment, the NSAID is a hydrophobic NSAID. In another embodiment, the NSAID is an amphipathic NSAID. In another embodiment, the matrix composition is in the form of a lipid-saturated matrix whose shape and boundaries are determined by the biodegradable polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) biodegradable polyester; (b) a sterol; (c) a phosphatidylethanolamine having fatty acid moieties of at least 14 carbons; (d) a phosphatidylcholine having fatty acid moieties of at least 14 carbons; and (e) an osteogenic factor or a bone resorption inhibitor. In another embodiment, the matrix composition is lipid saturated. Preferably, the polyester, the phosphatidylethanolamine, and the sterol are incorporated into the matrix composition. In another embodiment, the phosphatidylcholine is also incorporated into the matrix composition. In another embodiment, the bone resorption inhibitor is also incorporated into the matrix composition. In another embodiment, the bone resorption inhibitor has low water solubility. In another embodiment, the bone resorption inhibitor is a hydrophobic bone resorption inhibitor. In another embodiment, the bone resorption inhibitor is an amphipathic bone resorption inhibitor. In another embodiment, the composition further comprises an NSAID. In another embodiment, the NSAID as well is incorporated into the matrix composition. In another embodiment, the matrix composition is in the form of a lipid-saturated matrix whose shape and boundaries are determined by the biodegradable polymer. In another embodiment, the matrix composition is in the form of an implant. In another embodiment, the matrix composition is homogeneous. Each possibility represents a separate embodiment of the present invention.

In another embodiment, the present invention provides a matrix composition comprising: (a) biodegradable polyester; (b) a sterol; (c) a phosphatidylethanolamine having fatty acid moieties of at least 14 carbons, (d) a phosphatidylcholine having fatty acid moieties of at least 14 carbons; (e) an active agent; and (f) a targeting moiety capable of interacting with a surface molecule of a target cell, a target molecule or a target surface. In another embodiment, the matrix composition is lipid saturated. In another embodiment, the active agent is selected from the group consisting of an NSAID, an antibiotic, and a bone resorption inhibitor. In another embodiment, the polymer and the phospholipid form the matrix composition that is substantially free of water. In another embodiment, the active agent and the targeting moiety are integrated into the lipid vesicle. In another embodiment, the matrix composition is in the form of a lipid-saturated matrix whose shape and boundaries are determined by the biodegradable polymer. In another embodiment, the matrix composition is in the form of an implant. In another embodiment, the matrix composition is homogeneous. Each possibility represents a separate embodiment of the present invention.

In another embodiment, the biodegradable polyester of methods and compositions of the present invention is associated with the sterol via hydrogen bonds.

As provided herein, the matrix composition of methods and compositions of the present invention is capable of being molded into three-dimensional configurations of varying thickness and shape. Accordingly, the matrix formed can be produced to assume a specific shape including a sphere, cube, rod, tube, sheet, or into strings. In the case of freeze-drying, the shape is determined by the shape of a mold or support which may be made of any inert material and may be in contact with the matrix on all sides, as for a sphere or cube, or on a limited number of sides as for a sheet. The matrix may be shaped in the form of body cavities as required for implant design. Removing portions of the matrix with scissors, a scalpel, a laser beam or any other cutting instrument can create any refinements required in the three-dimensional structure. Each possibility represents a separate embodiment of the present invention.

Advantageously, the matrix compositions of the present invention are prepared by methods which do not involve the formation of emulsions, and may avoid the use of aqueous media altogether. The generation of emulsions that are subsequently dried necessarily results in vesicles or microspheres. In contrast, the matrices produced without aqueous media form homogeneous liquid mixtures that can be molded or formed into three dimensional articles of any shape or can coat the surface of different substrates. In order to produce molded or coated articles the mixture of polymer and lipids and active ingredients within the appropriate selected volatile organic solvents will be used to coat the desired surface or to fit the desired shape.

The matrix composition of methods and compositions of the present invention is capable of coating the surface of different substrates. Substrates to be coated include materials selected from the group consisting of carbon fibers, stainless steel, cobalt-chromium, titanium alloy, tantalum, ceramic and collagen or gelatin. Specifically, substrates may include any medical devices such as orthopedic nails, orthopedic screws, orthopedic staples, orthopedic wires and orthopedic pins used in orthopedic surgery, metal or polymeric implants used in both orthopedic and periodontal surgery, bone filler particles and absorbable gelatin sponge. Bone filler particles can be selected from any one of allogeneic (i.e., from human sources), xenogeneic (i.e., from animal sources) and artificial bone particles.

According to some embodiments, the matrix composition of the present invention is useful as a bone graft material. This term refers to a natural or synthetic material that supports attachment of new osteoblasts and osteoprogenitor cells or can induce non-differentiated stem cells or osteoprogenitor cells to differentiate into osteoblasts. In another embodiment, the bone graft material is selected from the group consisting of an allograft, an alloplast, a xenograft, and an autologous bone graft. In other example the lipid matrix of the present invention can also be used in conjunction with a collagen membrane or collagen sponge or gelatin sponge or the like.

Lipids

"Phospholipids" are phosphoglycerides having a single phosphatidyl linkage on a glycerol backbone and fatty acids at the remaining two positions. However, it is to be understood explicitly that phosphoglycerides having hydrocarbon chains other than fatty acid residues including alkyl chains, alkenyl chains or any other hydrocarbon chain of at least 14 carbons are included within the scope of the present invention. The linkage may be an ether linkage instead of an acyl linkage found in phospholipids.

"Phosphatidylcholine" refers to a phosphoglyceride having a phosphorylcholine head group. Phosphatidylcholine compounds, in another embodiment, have the following structure:

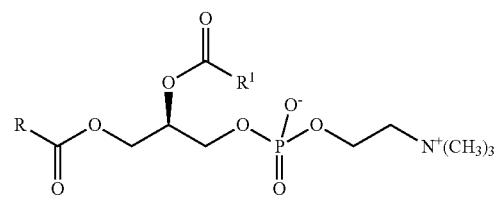

R and R¹ = fatty acids residues

The R and R' moieties are fatty acids, typically naturally occurring fatty acids or derivatives of naturally occurring fatty acids. In some embodiments, the fatty acid moieties are saturated fatty acid moieties. In some embodiments, the fatty acid moieties are unsaturated fatty acid moieties. "Saturated", refers to the absence of a double bond in the hydrocarbon chain. In another embodiment, the fatty acid moieties have at least 14 carbon atoms. In another embodiment, the fatty acid moieties have 16 carbon atoms. In another embodiment, the fatty acid moieties have 18 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are palmitoyl and stearoyl. In another embodiment, the fatty acid moieties are palmitoyl and arachidoyl. In another embodiment, the fatty acid moieties are arachidoyl and stearoyl. Each possibility represents a separate embodiment of the present invention.

In another embodiment, the phosphatidylcholine is a naturally-occurring phosphatidylcholine. In another embodiment, the phosphatidylcholine is a synthetic phosphatidylcholine. In another embodiment, the phosphatidylcholine contains a naturally-occurring distribution of isotopes. In another embodiment, the phosphatidylcholine is a deuterated phosphatidylcholine. In another embodiment, the phosphatidylcholine is labeled with any other isotope or label. Preferably, the phosphatidylcholine is a symmetric phosphatidylcholine (i.e. a phosphatidylcholine wherein the two fatty acid moieties are identical). In another embodiment, the phosphatidylcholine is an asymmetric phosphatidylcholine.

Non-limiting examples of phosphatidylcholines are 1,2-distearoyl-sn-glycero-3-phosphocholine (DSPC), dioleoyl-phosphocholine (DOPC), 1-palmitoyl-2-oleoyl-phosphatidylcholine, and phosphatidylcholines modified with any of the fatty acid moieties enumerated hereinabove. In another embodiment, the phosphatidylcholine is selected from the group consisting of DSPC and DOPC, and 1-palmitoyl-2-oleoyl-phosphatidylcholine.

In another embodiment, the phosphatidylcholine is any other phosphatidylcholine known in the art. Each phosphatidylcholine represents a separate embodiment of the present invention.

"Phosphatidylethanolamine" refers to a phosphoglyceride having a phosphoryl ethanolamine head group. Phosphatidylethanolamine compounds, in another embodiment, have the following structure:

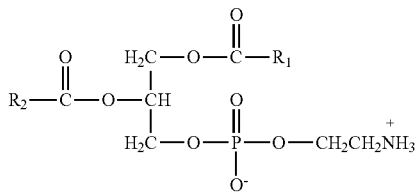

The $R_1$ and $R_2$ moieties are fatty acids, typically naturally occurring fatty acids or derivatives of naturally occurring fatty acids. In another embodiment, the fatty acid moieties are saturated fatty acid moieties. "Saturated" in another embodiment, refers to the absence of a double bond in the hydrocarbon chain. In another embodiment, the fatty acid moieties have at least 14 carbon atoms. In another embodiment, the fatty acid moieties have at least 16 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are myristoyl and arachidoyl. In another embodiment, the fatty acid moieties are myristoyl and palmitoyl. In another embodiment, the fatty acid moieties are palmitoyl and stearoyl. In another embodiment, the fatty acid moieties are palmitoyl and arachidoyl. In another embodiment, the fatty acid moieties are arachidoyl and stearoyl. Each possibility represents a separate embodiment of the present invention.

In another embodiment, the phosphatidylethanolamine is a naturally-occurring phosphatidylethanolamine. In another embodiment, the phosphatidylethanolamine is a synthetic phosphatidylethanolamine. In another embodiment, the phosphatidylethanolamine is a deuterated phosphatidylethanolamine. In another embodiment, the phosphatidylethanolamine is labeled with any other isotope or label. In another embodiment, the phosphatidylethanolamine contains a naturally-occurring distribution of isotopes. Preferably, the phosphatidylethanolamine is a symmetric phosphatidylethanolamine. In another embodiment, the phosphatidylethanolamine is an asymmetric phosphatidylethanolamine.

Non-limiting examples of phosphatidylethanolamines are dimethyl dimyristoyl phosphatidylethanolamine (DMPE) and dipalmitoyl-phosphatidylethanolamine (DPPE), and phosphatidylethanolamines modified with any of the fatty acid moieties enumerated hereinabove. In another embodiment, the phosphatidylethanolamine is selected from the group consisting of DMPE and DPPE.

In another embodiment, the phosphatidylethanolamine is any other phosphatidylethanolamine known in the art. Each phosphatidylethanolamine represents a separate embodiment of the present invention.

"Sterol" in one embodiment refers to a steroid with a hydroxyl group at the 3-position of the A-ring. In another embodiment, the term refers to a steroid having the following structure:

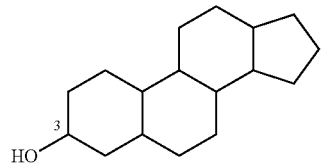 [SMILES: OC1CCC2C(CCC3C4CCCC4CCC23)C1]

In another embodiment, the sterol of methods and compositions of the present invention is a zoosterol. In another embodiment, the sterol is cholesterol:

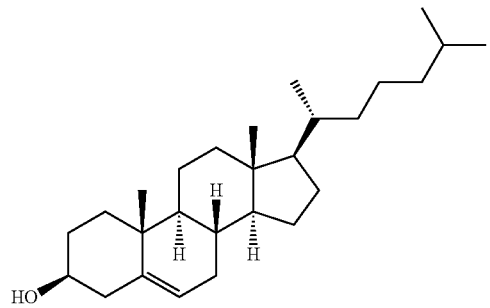

In another embodiment, the sterol is any other zoosterol known in the art. In another embodiment, the moles of sterol are up to 40% of the moles of total lipids present. In another embodiment, the sterol is incorporated into the matrix composition. Each possibility represents a separate embodiment of the present invention.

In another embodiment, the cholesterol is present in an amount of 10-50 percentage of the total weight of lipid content of the matrix composition. In another embodiment, the weight percentage is 20-50%. In another embodiment, the weight percentage is 10-40%. In another embodiment, the weight percentage is 30-50%. In another embodiment, the weight percentage is 20-60%. In another embodiment, the weight percentage is 25-55%. In another embodiment, the weight percentage is 35-55%. In another embodiment, the weight percentage is 30-60%. In another embodiment, the weight percentage is 30-55%. In another embodiment, the weight percentage is 20-50%. In another embodiment, the weight percentage is 25-55%. Each possibility represents a separate embodiment of the present invention.

In another embodiment, a composition of the present invention further comprises a lipid other than phosphatidylcholine, phosphatidylethanolamine, or a sterol. In another embodiment, the additional lipid is a phosphoglyceride. In another embodiment, the additional lipid is selected from the group consisting of a phosphatidylserine, a phosphatidylglycerol, and a phosphatidylinositol. In another embodiment, the additional lipid is selected from the group consisting of a phosphatidylserine, a phosphatidylglycerol, a phosphatidylinositol, and a sphingomyelin. In another embodiment, a combination of any 2 or more of the above additional lipids is present. In another embodiment, the polymer, phosphatidylcholine, phosphatidylethanolamine, sterol, and additional lipid(s) are all incorporated into the matrix composition. Each possibility represents a separate embodiment of the present invention.

In another embodiment, phosphatidylcholine(s) (PC) compose at least 30% of the total lipid content of the matrix composition. In another embodiment, PC(s) compose at least 35% of the total lipid content. In another embodiment, PC(s) compose at least 40% of the total lipid content. In another embodiment, PC(s) compose at least 45% of the total lipid content. In another embodiment, PC(s) compose at least 50% of the total lipid content. In another embodiment, PC(s) compose at least 55% of the total lipid content. In another embodiment, PC(s) compose at least 60% of the total lipid content. In another embodiment, PC(s) compose at least 65% of the total lipid content. In another embodiment, PC(s) compose at least 70% of the total lipid content. In another embodiment, PC(s) compose at least 75% of the total lipid content. In another embodiment, PC(s) compose at least 80% of the total lipid content. In another embodiment, PC(s) compose at least 85% of the total lipid content. In another embodiment, PC(s) compose at least 90% of the total lipid content. In another embodiment, PC(s) compose at least 95% of the total lipid content. In another embodiment, PC(s) compose over 95% of the total lipid content. Each possibility represents a separate embodiment of the present invention.

In another embodiment, a composition of the present invention further comprises a phosphatidylserine. "Phosphatidylserine" refers to a phosphoglyceride having a phosphorylserine head group. Phosphatidylserine compounds, in another embodiment, have the following structure:

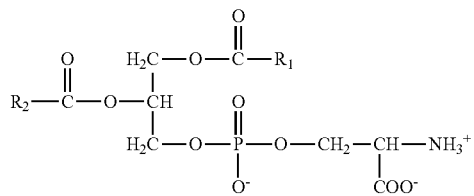

The $R_1$ and $R_2$ moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

In another embodiment, the phosphatidylserine is a naturally-occurring phosphatidyl serine. In another embodiment, the phosphatidylserine is a synthetic phosphatidyl serine. In another embodiment, the phosphatidylserine is a deuterated phosphatidyl serine. In another embodiment, the phosphatidylserine is labeled with any other isotope or label. In another embodiment, the phosphatidylserine contains a naturally-occurring distribution of isotopes. In another embodiment, the phosphatidylserine is a symmetric phosphatidylserine. In another embodiment, the phosphatidylserine is an asymmetric phosphatidylserine.

Non-limiting examples of phosphatidylserines are phosphatidylserines modified with any of the fatty acid moieties enumerated hereinabove. In another embodiment, the phosphatidylserine is any other phosphatidylserine known in the art. Each phosphatidylserine represents a separate embodiment of the present invention.

In another embodiment, a composition of the present invention further comprises a phosphatidylglycerol. "Phosphatidylglycerol" refers to a phosphoglyceride having a phosphoryl glycerol head group. Phosphatidylglycerol compounds, in another embodiment, have the following structure:

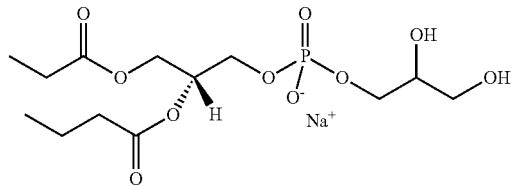 [SMILES: CCCC(=O)O[C@H](COC(=O)CC)COP(=O)([O-])OCC(O)CO ; [Na+]]

The 2 bonds to the left are connected to fatty acids, typically naturally occurring fatty acids or derivatives of naturally occurring fatty acids. In another embodiment, the phosphatidylglycerol is a naturally-occurring phosphatidylglycerol. In another embodiment, the phosphatidylglycerol is a synthetic phosphatidyl glycerol. In another embodiment, the phosphatidylglycerol is a deuterated phosphatidylglycerol. In another embodiment, the phosphatidylglycerol is labeled with any other isotope or label. In another embodiment, the phosphatidylglycerol contains a naturally-occurring distribution of isotopes. In another embodiment, the phosphatidylglycerol is a symmetric phosphatidylglycerol. In another embodiment, the phosphatidylglycerol is an asymmetric phosphatidylglycerol. In another embodiment, the term includes diphosphatidylglycerol compounds having the following structure:

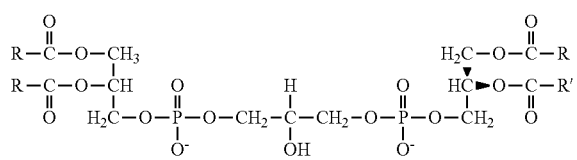

The R and R' moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

Non-limiting examples of phosphatidylglycerols are phosphatidylglycerols modified with any of the fatty acid moieties enumerated hereinabove. In another embodiment, the phosphatidylglycerol is any other phosphatidylglycerol known in the art. Each phosphatidylglycerol represents a separate embodiment of the present invention.

In another embodiment, a composition of the present invention further comprises a phosphatidylinositol. "Phosphatidyl inositol" refers to a phosphoglyceride having a phosphorylinositol head group. Phosphatidylinositol compounds, in another embodiment, have the following structure:

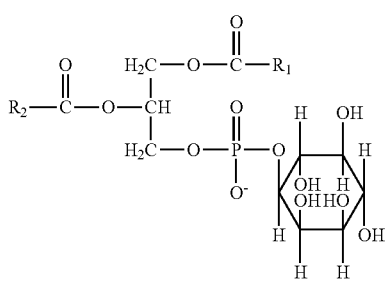

The $R_1$ and $R_2$ moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

In another embodiment, the phosphatidyl inositol is a naturally-occurring phosphatidylinositol. In another embodiment, the phosphatidylinositol is a synthetic phosphatidylinositol. In another embodiment, the phosphatidylinositol is a deuterated phosphatidylinositol. In another embodiment, the phosphatidylinositol is labeled with any other isotope or label. In another embodiment, the phosphatidylinositol contains a naturally-occurring distribution of isotopes. In another embodiment, the phosphatidylinositol is a symmetric phosphatidylinositol. In another embodiment, the phosphatidylinositol is an asymmetric phosphatidylinositol.

Non-limiting examples of phosphatidylinositols are phosphatidylinositols modified with any of the fatty acid moieties enumerated hereinabove. In another embodiment, the phosphatidylinositol is any other phosphatidylinositol known in the art. Each phosphatidylinositol represents a separate embodiment of the present invention.

In another embodiment, a composition of the present invention further comprises a sphingolipid. In another embodiment, the sphingolipid is ceramide. In another embodiment, the sphingolipid is a sphingomyelin. "Sphingomyelin" refers to a sphingosine-derived phospholipid. Sphingomyelin compounds, in another embodiment, have the following structure:

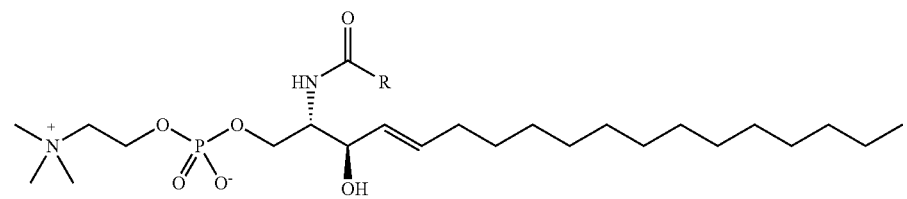

The R moiety is a fatty acid, typically a naturally occurring fatty acid or a derivative of a naturally occurring fatty acid. In another embodiment, the sphingomyelin is a naturally-occurring sphingomyelin. In another embodiment, the sphingomyelin is a synthetic sphingomyelin. In another embodiment, the sphingomyelin is a deuterated sphingomyelin. In another embodiment, the sphingomyelin is labeled with any other isotope or label. In another embodiment, the sphingomyelin contains a naturally-occurring distribution of isotopes.

In another embodiment, the fatty acid moiety of a sphingomyelin of methods and compositions of the present invention has at least 14 carbon atoms. In another embodiment, the fatty acid moiety has at least 16 carbon atoms. In another embodiment, the fatty acid moiety is chosen such that the gel-to-liquid-crystal transition temperature of the resulting matrix is at least 40° C.

Non-limiting examples of sphingomyelins are sphingomyelins modified with any of the fatty acid moieties enumerated hereinabove. In another embodiment, the sphingomyelin is any other sphingomyelin known in the art. Each sphingomyelin represents a separate embodiment of the present invention.

"Ceramide" refers to a compound having the structure:

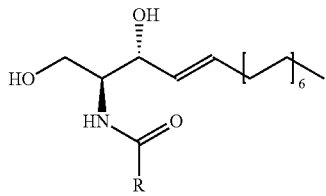

The R moiety is a fatty acid typically naturally occurring fatty acid or derivatives of naturally occurring fatty acids. In another embodiment, the fatty acid is a longer-chain (to $C_{24}$ or greater). In another embodiment, the fatty acids are saturated fatty acids. In another embodiment, the fatty acids are monoenoic fatty acids. In another embodiment, the fatty acids are n-9 monoenoic fatty acids. In another embodiment, the fatty acids contain a hydroxyl group in position 2. In another embodiment, the fatty acids are other suitable fatty acids known in the art. In another embodiment, the ceramide is a naturally-occurring ceramide. In another embodiment, the ceramide is a synthetic ceramide. In another embodiment, the ceramide is incorporated into the matrix composition. Each possibility represents a separate embodiment of the present invention.

Each sphingolipid represents a separate embodiment of the present invention.

In another embodiment, a composition of the present invention further comprises a pegylated lipid. In another embodiment, the PEG moiety has a MW of 500-5000 daltons. In another embodiment, the PEG moiety has any other suitable MW. Non-limiting examples of suitable PEG-modified lipids include PEG moieties with a methoxy end group, e.g. PEG-modified phosphatidylethanolamine and phosphatidic acid (structures A and B), PEG-modified diacylglycerols and dialkylglycerols (structures C and D), PEG-modified dialkylamines (structure E) and PEG-modified 1,2-diacyloxypropan-3-amines (structure F) as depicted below. In another embodiment, the PEG moiety has any other end group used in the art. In another embodiment, the pegylated lipid is selected from the group consisting of a PEG-modified phosphatidylethanolamine, a PEG-modified phosphatidic acid, a PEG-modified diacylglycerol, a PEG-modified dialkylglycerol, a PEG-modified dialkylamine, and a PEG-modified 1,2-diacyloxypropan-3-amine. In another embodiment, the pegylated lipid is any other pegylated phospholipid known in the art. Each possibility represents a separate embodiment of the present invention.

A

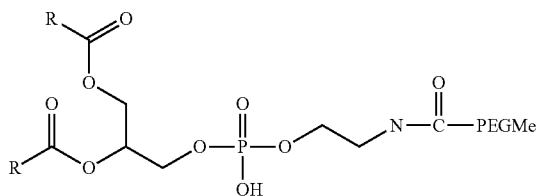

B

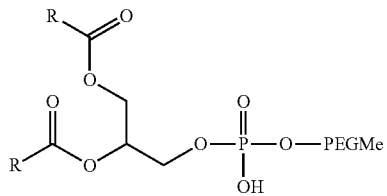

C

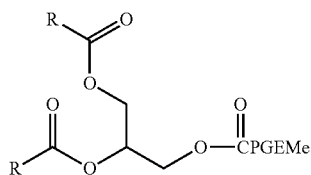

D

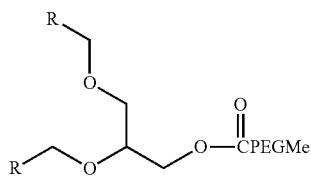

E

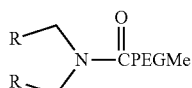

F

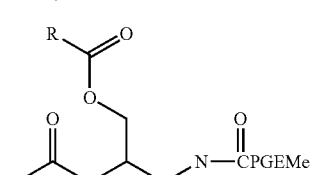

Preferably, the pegylated lipid is present in an amount of less than 10 mole percent of total lipids in the matrix composition. In another embodiment, the percentage is less than 9 mole % of the total lipids. In another embodiment, the percentage is less than 8 mole %. In another embodiment, the percentage is less than 7 mole %. In another embodiment, the percentage is less than 6 mole %. In another embodiment, the percentage is less than 5 mole %. In another embodiment, the percentage is less than 4 mole %. In another embodiment, the percentage is less than 3 mole %. In another embodiment, the percentage is less than 2 mole %. In another embodiment, the percentage is less than 1 mole %. Each possibility represents a separate embodiment of the present invention.

Polymers

The biodegradable polyester of methods and compositions of the present invention is, in another embodiment, PLA (polylactic acid). "PLA" refers to poly(L-lactide), poly(D-lactide), and poly(DL-lactide). A representative structure of poly(DL-lactide) is depicted below:

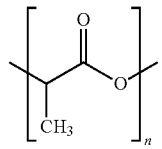

In another embodiment, the polymer is PGA (polyglycolic acid). In another embodiment, the polymer is PLGA (poly (lactic-co-glycolic acid). The PLA contained in the PLGA may be any PLA known in the art, e.g. either enantiomer or a racemic mixture. A representative structure of PLGA is depicted below:

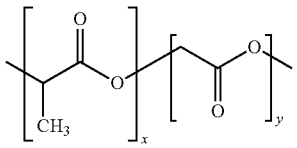

The PLGA of methods and compositions of the present invention has, in another embodiment, a 1:1 lactic acid/glycolic acid ratio. In another embodiment, the ratio is 60:40. In another embodiment, the ratio is 70:30. In another embodiment, the ratio is 80:20. In another embodiment, the ratio is 90:10. In another embodiment, the ratio is 95:5. In another embodiment, the ratio is another ratio appropriate for an extended in vivo release profile, as defined herein. In another embodiment, the ratio is 50:50. The PLGA may be either a random or block copolymer. Each possibility represents a separate embodiment of the present invention.

In another embodiment, the biodegradable polyester is selected from the group consisting of a polycaprolactone, a polyhydroxyalkanoate, a polypropylenefumarate, a polyorthoester, a polyanhydride, and a polyalkylcyanoacrylate, provided that the polyester contains a hydrogen bond acceptor moiety. In another embodiment, the biodegradable polyester is a block copolymer containing a combination of any two monomers selected from the group consisting of a PLA, PGA, a PLGA, polycaprolactone, a polyhydroxyalkanoate, a polypropylenefumarate, a polyorthoester, a polyanhydride, and a polyalkylcyanoacrylate. In another embodiment, the biodegradable polyester is a random copolymer containing a combination of any two of the monomers listed above. Each possibility represents a separate embodiment of the present invention.

The molecular weight (MW) of a biodegradable polyester of methods and compositions of the present invention is, in another embodiment, between about 10-40 KDa. In another embodiment, the MW is between about 5-50 KDa. In another embodiment, the MW is between about 15-40 KDa. In another embodiment, the MW is between about 20-40 KDa. In another embodiment, the MW is between about 15-35 KDa. In another embodiment, the MW is between about 10-35 KDa. In another embodiment, the MW is between about 10-30 KDa. In another embodiment, a mixture of PLGA polymers of different MW is utilized. In another embodiment, the different polymers both have a MW in one of the above ranges. Each possibility represents a separate embodiment of the present invention.

Antibiotics

The antibiotic of methods and compositions of the present invention is, in another embodiment, doxycycline. In another embodiment, the antibiotic is a hydrophobic tetracycline. Non-limiting examples of hydrophobic tetracycline are 6-demethyl-6-deoxytetracycline, 6-methylene tetracycline, minocycline (also known as 7-dimethylamino-6-demethyl-6-deoxytetracycline), and 13-phenylmercapto-a-6-deoxytetracycline. In another embodiment, the antibiotic is selected from the group consisting of doxycycline, tetracycline, and minocycline. In another embodiment, the antibiotic is integrated into the matrix composition.

In another embodiment, the antibiotic is selected from the group consisting of amoxicillin, amoxicillin/clavulanic acid, penicillin, metronidazole, clindamycine, chlortetracycline, demeclocycline, oxytetracycline, amikacin, gentamicine, kanamycin, neomycin, netilmicin, streptomycin, tobramycin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, chloramphenicol, clofazimine, colistimethate, colistin, cycloserine, fosfomycin, furazolidone, methenamine, nitrofurantoin, pentamidine, rifabutin, rifampin, spectinomycin, trimethoprim, trimetrexate glucuronate, and vancomycin.

In another embodiment, the biologically active ingredient is an antiseptic drug such as chlorhexidine.

Each antibiotic represents a separate embodiment of the present invention.

NSAID's

Any suitable NSAID may be integrated into the matrix composition for sustained and/or controlled release. The NSAID of methods and compositions of the present invention is, in one embodiment, flurbiprofen. In another embodiment, the NSAID is selected from the group consisting of ibuprofen and flurbiprofen. In another embodiment, the NSAID is selected from the group consisting of ibuprofen, flurbiprofen, aminosalicylate sodium, choline magnesium trisalicylate, choline salicylate, diclofenac, diflunisal, etodolac, fenoprofen, indomethacin, ketoprofen, ketolac tromethamine, magnesium salicylate, meclofenamate, mefenamic acid, nabumetone, naproxen, oxaprozin, oxyphenbutazone, piroxicam, salsalate, sulindac, tolmetin.

Each NSAID represents a separate embodiment of the present invention.

Steroids

In another embodiment, the active agent of methods and compositions of the present invention is a steroid. According to one embodiment the steroid is a steroidal anti-inflammatory drug. Non limiting examples of steroidal anti-inflammatory drugs (SAIDs) to be used in the formulations of the present invention include, but are not limited to, Corticosteroids such as: betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide, cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, diflupred-nate, flucloronide, flumethasone pivalate, flunisolide acetate, fluperolone acetate, fluprednisolone valerate, parametha-sone acetate, prednisolamate, prednival, triamcinolone hexacetonide, cortivazol, formocortal and nivazol.

Anti-Cancer Agents

As referred to herein, the term "anti-cancer agent" refers to any type of agent that may be used in the treatment of cancer and/or cancer related conditions. The anti-cancer reagent may include any naturally occurring or synthetically produced molecule that is capable of affecting directly or indirectly the growth and/or viability of cancer cells, cancer tumor, and/or cancer related conditions and symptoms. The anti-cancer agent may include, for example, a naturally occurring protein or peptide, a modified protein or peptide, a recombinant protein, a chemically synthesized protein or peptide, a low oral bioavailability protein or peptide, a chemical molecule, a synthetic chemical molecule, a che-motherapeutic drug, a biologically therapeutic drug, and the like, or any combination thereof. The anti-cancer reagent may be cytotoxic (toxic to cells) and/or cytostatic (suppress cell growth) and/or antiproliferative to the cancer cells and may exert its effect on cancer cells directly and/or indirectly. According to some embodiments, the anti-cancer reagent may be administered alone and/or in combination and/or before and/or after one or more additional cancer treatments. The additional cancer treatment may include such treatments as, but not limited to: chemotherapy (use of drugs to affect the cancer cells), radiotherapy (use of high-energy radiation of various sources to affect the cancer cells); biological therapy (a therapy which helps the immune system fight cancer); surgical procedures (surgical removal of the can-cerous tumor); gene therapy; bone marrow transplantation; any other therapy known in the art, or any combination thereof.

Non limiting examples of anti-cancer reagents and che-motherapeutic drugs may include such drugs as, but not limited to: Alkaloids, such as, but not limited to: Docetaxel, Etoposide, Irinotecan, Paclitaxel, Teniposide, Topotecan, Vinblastine, Vincristine, Vindesine; Alkylating agents, such as, but not limited to: Busulfan, Improsulfan, Piposulfan, Benzodepa, Carboquone, Meturedepa, Uredepa, Altret-amine, triethylenemelamine, Triethylenephosphoramide, Triethylenethiophosphoramide, Chlorambucil, Chlornap-hazine, Cyclophosphamide, Estramustine, Ifosfamide, Mechlorethamine, Mechlorethamine Oxide Hcl, Melphalan, Novemebichin, Perfosfamide Phenesterine, Prednimustine, Trofosfamide, Uracil Mustard, Carmustine, Chlorozotocin, Fotemustine, Lomustine, Nimustine, Semustine Rani-mustine, Dacarbazine, Mannomustine, Mitobronitol, Mito-lactol, Pipobroman, Temozolomide; Antibiotics and analogs, such as, but not limited to: Aclacinomycins, Actinomycins, Anthramycin, Azaserine, Bleomycins, Cactinomycin, Caru-bicin, Carzinophilin, Cromomycins, Dactinomycins, Daunorubicin, 6-Diazo-5-oxo-L-norleucine, Doxorubicin, Epirubicin, Idarubicin, Menogaril, Mitomycins, Mycophe-nolic Acid, Nogalamycine, Olivomycins, Peplomycin, Pira-rubicin, Plicamycin, Porfiromycin, Puromycine, Streptoni-grin, Streptozocin, Tubercidin, Zinostatin, Zorubicin; Antimetabolites, such as, but not limited to: Denopterin, Edatrexate, Methotrexate, Piritrexim, Pteropterin, Tomudex, Trimetrexate, Cladridine, Fludarabine, 6-Mercaptopurine, Pentostatine Thiamiprine, Thioguanine, Ancitabine, Azaciti-dine, 6-Azauridine, Carmofur, Cytarabine, Doxifluridine, Emitefur, Floxuridine, Fluorouracil, Gemcitabine, Tegafur; Platinum complexes, such as, but not limited to: Caroplatin, Cisplatin, Miboplatin, Oxaliplatin; alkylators including, but not limited to, busulfan (Myleran, Busulfex), chlorambucil (Leukeran), ifosfamide (with or without MESNA), cyclo-phosphamide (Cytoxan, Neosar), glufosfamide, melphalan, L-PAM (Alkeran), dacarbazine (DTIC-Dome), and temozo-lamide (Temodar); anthracyclines, including, but not limited to doxorubicin (Adriamycin, Doxil, Rubex), mitoxantrone (Novantrone), idarubicin (Idamycin), valrubicin (Valstar), and epirubicin (Ellence); antibiotics, including, but not limited to, dactinomycin, actinomycin D (Cosmegen), bleo-mycin (Blenoxane), daunorubicin, and daunomycin (Ceru-bidine, DanuoXome); aromatase inhibitors, including, but not limited to anastrozole (Arimidex) and letroazole (Fe-mara); bisphosphonates, including, but not limited to zole-dronate (Zometa); cyclo-oxygenase inhibitors, including, but not limited to, celecoxib (Celebrex); estrogen receptor modulators including, but not limited to tamoxifen (Nolva-dex) and fulvestrant (Faslodex); folate antagonists includ-ing, but not limited to methotrexate and tremetrexate; inor-ganic aresenatesincluding, but not limited to arsenic trioxide (Trisenox); microtubule inhibitors (e.g. taxanes) including, but not limited to vincristine (Oncovin), vinblastine (Vel-ban), paclitaxel (Taxol, Paxene), vinorelbine (Navelbine), epothilone B or D or a derivative of either, and discoder-molide or its derivatives, nitrosoureas including, but not limited to procarbazine (Matulane), lomustine, CCNU (CeeBU), carmustine (BCNU, BiCNU, Gliadel Wafer), and estramustine (Emcyt); nucleoside analogs including, but not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), pentostatin (Ni-pent), cladribine (Leustatin, 2-CdA), gemcitabine (Gemzar), and capecitabine (Xeloda); osteoclast inhibitors including, but not limited to pamidronate (Aredia); platinum containing compounds including, but not limited to cisplatin (Platinol) and carboplatin (Paraplatin); retinoids including, but not limited to tretinoin, ATRA (Vesanoid), alitretinoin (Panre-tin), and bexarotene (Targretin); topoisomerase 1 inhibitors including, but not limited to topotecan (Hycamtin) and irinotecan (Camptostar); topoisomerase 2 inhibitors includ-ing, but not limited to etoposide, VP-16 (Vepesid), tenipo-side, VM-26 (Vumon), and etoposide phosphate (Etopo-phos); tyrosine kinase inhibitors including, but not limited to imatinib (Gleevec); various other proteins including mono-clonal antibodies, peptides and enzymes, various other mol-ecules, such as, for example, Super Oxide dismutase (SOD), leptin; flavanoids; or any combinations thereof.

Non limiting examples of anti-cancer agents and biologi-cal therapies that may be used according to some embodi-ments, may include, such therapies and molecules as, but not limited to: administration of an immunomodulatory mol-ecule, such as, for example, a molecule selected from the group consisting of tumor antigens, antibodies, cytokines (such as, for example, interleukins (such as, for example, interleukin 2, interleukin 4, interleukin 12), interferons (such as, for example, interferon El interferon D, interferon alpha), tumor necrosis factor (TNF), granulocyte macrophage colony stimulating factor (GM-CSF), macrophage colony stimulating factor (M-CSF), and granulocyte colony stimu-lating factor (G-CSF)), tumor suppressor genes, chemok-ines, complement components, complement component receptors, immune system accessory molecules, adhesion molecules, adhesion molecule receptors, agents affecting cell bioenergetics, or any combinations thereof.

Osteogenic Factors

In another embodiment, the active agent of methods and compositions of the present invention is a compound which induces or stimulates the formation of bone. In another embodiment the active agent is osteogenic factor. In another embodiment, the osteogenic factor refers to any peptide, polypeptide, protein or any other compound or composition which induces or stimulates the formation of bone. In another embodiment, the osteogenic factor induces differentiation of bone repair cells into bone cells, such as osteoblasts or osteocytes. In another embodiment the osteogenic factor is selected from the group consisting of TGF-beta, BMP and FGF. In another embodiment the osteogenic factor is encapsulated within the matrix composition of the present invention in a concentration sufficient to induce differentiation of bone repair cells into bone cells which form bone.

Bone Resorption Inhibitors

In another embodiment, the active agent of methods and compositions of the present invention is a compound useful for supporting bone recovery. In another embodiment, the active agent is a bone resorption inhibitor. In another embodiment, the active agent is a bone density conservation agent. In another embodiment, the compound is selected from the group consisting of osteoprotegerin (OPG), BMP-2, BMP-4, vascular endothelial growth factor (VEGF), alendronate, etidronate disodium, pamidronate, risedronate, and tiludronate. In another embodiment, the compound is osteoprotegerin (OPG), a naturally secreted decoy receptor that inhibits osteoclast maturation and activity and induces osteoclast apoptosis. In another embodiment, the active agent is a bone restructuring element. Non-limiting examples of bone restructuring elements are BMP peptides. Each possibility represents a separate embodiment of the present invention.

In another embodiment, the compound is a bone morphogenetic protein (BMP). In another embodiment, the compound is selected from the group consisting of BMP-2 and BMP-4, which accelerate osteoblast activity.

In another embodiment, the compound is vascular endothelial growth factor (VEGF).

In another embodiment, the compound is an estrogen. In another embodiment, the compound is selected from the group consisting of bisphosphonate derivative. In another embodiment, the bisphosphonate derivative is selected from the group consisting of alendronate, etidronate disodium, pamidronate, risedronate, and tiludronate.

Each compound represents a separate embodiment of the present invention.

Anti-Fungal Agents

In another embodiment, the biologically active ingredient is an antifungal drug, e.g. amphotericin B cholesteryl sulfate complex, natamycin, amphotericine, clotrimazole, nystatin, amphotericin B lipid complex, fluconazole, filucytosine, griseofulvin, itraconazole, ketoconazole, benzoic acid and salicylic acid, betamethasone and clotrimazole, butenafine, carbol-fuchsin, ciclopirox, clioquinol, clioquinol and hydrocortisone, clotrimazole, econazole, gentian violet, haloprogin, iodoquinol and hydrocortisone, ketoconazole, miconazole, naftifine, nystatin, nystatin and triamcinolone, oxiconazole, sodium thiosulfate, sulconazole, terbinafine, tolnaftate, triacetin, undecylenic acid and derivatives thereof, butoconazole, clotrimazole, sulfanilamide, terconazole, and tioconazole.

Targeting Moieties

In another embodiment, a matrix composition of methods and compositions of the present invention further comprises a targeting moiety capable of interacting with a target molecule. Preferably the target molecule is selected from the group consisting of a collagen molecule, a fibrin molecule and a heparin. In another embodiment, the target molecule is another surface molecule that forms part of the extracellular matrix (ECM) of a target cell. ECM is produced and assembled locally by cells. The most important cells involved in assembling and maintaining ECM are fibroblasts. ECM contains polysaccharide chains called GAGs (glyosaminoglycans) and various protein fibers e.g., collagen, elastin, fibronectin and laminin.

In another embodiment, the targeting moiety is a fibronectin peptide. Fibronectin is a high-molecular-weight glycoprotein that binds ECM components such as collagen, fibrin and heparin. In another embodiment, the targeting moiety is another targeting moiety capable of interaction with a target molecule selected from the group consisting of a collagen molecule, a fibrin molecule and a heparin. Each possibility represents a separate embodiment of the present invention.

"Fibronectin peptide" refers, in another embodiment, to a full-length fibronectin protein. In another embodiment, the term refers to a fragment of fibronectin. In another embodiment, the fragment includes the collagen binding domain. Collagen binding domains of fibronectin molecules are well known in the art, and are described, for example, in Hynes, RO (1990). Fibronectins. New York: Springer-Verlag and in Yamada, K M and Clark, R A F (1996). Provisional matrix. In The Molecular and Cellular Biology of Wound Repair (ed. R. A. F. Clark), pp. 51-93. New York: Plenum Press. Each possibility represents a separate embodiment of the present invention.

In another embodiment, the targeting moiety is incorporated into the matrix composition. In another embodiment, the targeting moiety is modified to confer ability to incorporate into the lipid matrix. In another embodiment, the modification comprises binding to a lipid moiety. A non-limiting example of a lipid moiety is hydrogenated phosphatidylethanolamine (HPE). However, any lipid moiety capable of incorporation into the lipid matrix is suitable. In another embodiment, the targeting moiety is able to be incorporated into the lipid matrix without modification. In another embodiment, the targeting moiety is attached to the surface of a matrix composition of the present invention. In another embodiment, the targeting moiety is bound to the surface of the matrix composition or vesicle by a hydrophobic anchor covalently bound to the targeting moiety. In another embodiment, the targeting moiety is bound to the lipid vesicles by a hydrophobic anchor. In another embodiment, the targeting moiety is included during the preparation of the drug carrier, allowing it to be located in deeper layers of the carrier. Each possibility represents a separate embodiment of the present invention.

In one embodiment, the target molecule is a collagen. Collagens are well known in the art, and are described, for example, in Khoshnoodi J et al (Molecular recognition in the assembly of collagens: terminal noncollagenous domains are key recognition modules in the formation of triple helical protomers. J Biol Chem. 281(50):38117-21, 2006). Each possibility represents a separate embodiment of the present invention.

In one embodiment, the target molecule is a fibrin. Fibrins are well known in the art, and are described, for example, in Valenick L V et al (Fibronectin fragmentation promotes alpha4beta1 integrin-mediated contraction of a fibrin-fibronectin provisional matrix. Exp Cell Res 309(1):48-55, 2005) and Mosesson M W (Fibrinogen and fibrin structure and functions. J Thromb Haemost 3(8):1894-904, 2005). Each possibility represents a separate embodiment of the present invention.

In one embodiment, the target molecule is a heparin. Heparins are well known in the art, and are described, for example, in Mosesson M W (Fibrinogen and fibrin structure and functions. J Thromb Haemost 3(8):1894-904, 2005). Each possibility represents a separate embodiment of the present invention.

Additional Components

In another embodiment, a matrix composition of methods and compositions of the present invention further comprises a free fatty acid. In another embodiment, the free fatty acid is an omega-6 fatty acid. In another embodiment, the free fatty acid is an omega-9 fatty acid. In another embodiment, the free fatty acid is selected from the group consisting of omega-6 and omega-9 fatty acids. In another embodiment, the free fatty acid has 14 or more carbon atoms. In another embodiment, the free fatty acid has 16 or more carbon atoms. In another embodiment, the free fatty acid has 16 carbon atoms. In another embodiment, the free fatty acid has 18 carbon atoms. In another embodiment, the free fatty acid has 16-22 carbon atoms. In another embodiment, the free fatty acid has 16-20 carbon atoms. In another embodiment, the free fatty acid has 16-18 carbon atoms. In another embodiment, the free fatty acid has 18-22 carbon atoms. In another embodiment, the free fatty acid has 18-20 carbon atoms. In another embodiment, the free fatty acid is linoleic acid. In another embodiment, the free fatty acid is linolenic acid. In another embodiment, the free fatty acid is oleic acid. In another embodiment, the free fatty acid is selected from the group consisting of linoleic acid, linolenic acid, and oleic acid. In another embodiment, the free fatty acid is another appropriate free fatty acid known in the art. In another embodiment, the free fatty acid adds flexibility to the matrix composition. In another embodiment, the free fatty acid slows the in vivo release rate. In another embodiment, the free fatty acid improves the consistency of the in vivo controlled release. In some embodiments the fatty acid is unsaturated. In another embodiment, the free fatty acid is saturated. In another embodiment, incorporation of a saturated fatty acid having at least 14 carbon atoms increases the gel-fluid transition temperature of the resulting matrix composition.

In another embodiment, the free fatty acid is deuterated. In another embodiment, deuteration of the lipid acyl chains lowers the gel-fluid transition temperature.

In another embodiment, a free fatty acid is incorporated into the matrix composition. Each type of fatty acid represents a separate embodiment of the present invention.

In another embodiment, a matrix composition of methods and compositions of the present invention further comprises a tocopherol. The tocopherol of methods and compositions of the present invention is, in another embodiment, E307 (α-tocopherol). In another embodiment, the tocopherol is β-tocopherol. In another embodiment, the tocopherol is E308 (γ-tocopherol). In another embodiment, the tocopherol is E309 (δ-tocopherol). In another embodiment, the tocopherol is selected from the group consisting of α-tocopherol, β-tocopherol, γ-tocopherol, and δ-tocopherol. In another embodiment, the tocopherol is incorporated into the matrix composition. Each possibility represents a separate embodiment of the present invention.

In another embodiment, a matrix composition of methods and compositions of the present invention further comprises physiologically acceptable buffer salts, which are well known in the art. Non-limiting examples of physiologically acceptable buffer salts are phosphate buffers. A typical example of a phosphate buffer is 40 parts NaCl, 1 part KCl, 7 parts $Na_2HPO_4 \cdot 2H_2O$ and 1 part $KH_2PO_4$. In another embodiment, the buffer salt is any other physiologically acceptable buffer salt known in the art. Each possibility represents a separate embodiment of the present invention.

Release Rates and General Characteristics of the Matrix Compositions

The in vivo release time of 90% of the active ingredient for matrix compositions of the present invention is preferably between 1 week and 6 months. In another embodiment, the release time is between 4 days and 6 months. In another embodiment, the release time is between 1 week and 5 months. In another embodiment, the release time is between 1 week and 5 months. In another embodiment, the release time is between 1 week and 4 months. In another embodiment, the release time is between 1 week and 3 months. In another embodiment, the release time is between 1 week and 2 months. In another embodiment, the release time is between 2 weeks and 6 months. In another embodiment, the release time is between 2 weeks and 5 months. In another embodiment, the release time is between 2 weeks and 4 months. In another embodiment, the release time is between 2 weeks and 3 months. In another embodiment, the release time is between 3 weeks and 6 months. In another embodiment, the release time is between 3 weeks and 5 months. In another embodiment, the release time is between 3 weeks and 4 months. In another embodiment, the release time is between 3 weeks and 3 months. Each possibility represents a separate embodiment of the present invention.

Methods for modulating the release rate of biodegradable polymer implants (in the absence of lipids) and drug-containing vesicles (in the absence of biodegradable polymer) are well known in the art. For example, in the case of polymers, increasing the lactic acid:co-glycolic acid ratio of PLGA will extend the release time. In the case of drug-containing vesicles, increasing the amount of cholesterol will extend the release time. Each of these methods can be used to modulate the release rate of the matrix compositions of the present invention.

"Biodegradable," as used herein, refers to a substance capable of being decomposed by natural biological processes at physiological pH. "Physiological pH" refers to the pH of body tissue, typically between 6-8. "Physiological pH" does not refer to the highly acidic pH of gastric juices, which is typically between 1 and 3.

The weight ratio of total lipids to the polymer in order to achieve lipid saturation can be determined by a number of methods, as described herein. In another embodiment, the lipid:polymer weight ratio of a composition of the present invention is between 1:1 and 9:1 inclusive. In another embodiment, the ratio is between 2:1 and 9:1 inclusive. In another embodiment, the ratio is between 3:1 and 9:1 inclusive. In another embodiment, the ratio is between 4:1 and 9:1 inclusive. In another embodiment, the ratio is between 5:1 and 9:1 inclusive. In another embodiment, the ratio is between 6:1 and 9:1 inclusive. In another embodiment, the ratio is between 7:1 and 9:1 inclusive. In another embodiment, the ratio is between 8:1 and 9:1 inclusive. In another embodiment, the ratio is between 1.5:1 and 9:1 inclusive. Each possibility represents a separate embodiment of the present invention.

In another embodiment for purposes of illustration, in the case wherein the polymer is predominantly 40 KDa PLGA (poly (lactic-co-glycolic acid, 1:1 ratio)), the molar ratio of total lipids to 40 KDa PLGA is typically in the range of 20-100 inclusive. In another embodiment, the molar ratio of total lipids to 40 KDa PLGA is between 20-200 inclusive. In another embodiment, the molar ratio is between 10-100 inclusive. In another embodiment, the molar ratio is between 10-200 inclusive. In another embodiment, the molar ratio is between 10-50 inclusive. In another embodiment, the molar ratio is between 20-50 inclusive. Each possibility represents a separate embodiment of the present invention.

In another embodiment, the melting temperature ($T_m$) of a matrix composition of the present invention is at least 37° C. In another embodiment, the $T_m$ is at least 40° C. In another embodiment, the $T_m$ is at least 42° C. In another embodiment, the $T_m$ is at least 44° C. In another embodiment, the $T_m$ is at least 46° C. In another embodiment, the $T_m$ is at least 48° C. In another embodiment, the $T_m$ is at least 50° C. Each possibility represents a separate embodiment of the present invention.

Implants and Other Pharmaceutical Compositions

In another embodiment, a matrix composition of the present invention is in the form of an implant, following evaporation of the organic solvents. The evaporation of the solvents is typically done at temperatures ranging from 20 to 60° C.

In another embodiment, the implant is homogeneous. In another embodiment, the implant is manufactured by a process comprising the step of freeze-drying the material in a mold. Each possibility represents a separate embodiment of the present invention.

In another embodiment, the present invention provides an implant comprising an antibiotic-containing matrix composition of the present invention. In another embodiment, the present invention provides an implant comprising an NSAID-containing matrix composition of the present invention. In another embodiment, the present invention provides an implant comprising a bone resorption inhibitor-containing matrix composition of the present invention. In another embodiment, the present invention provides an implant comprising a matrix composition of the present invention that contains an antibiotic and an NSAID. In another embodiment, the present invention provides an implant comprising a matrix composition of the present invention that contains an antibiotic and a bone resorption inhibitor. In another embodiment, the present invention provides an implant comprising a matrix composition of the present invention that contains a bone resorption inhibitor and an NSAID. In another embodiment, the present invention provides an implant comprising a matrix composition of the present invention that contains an antibiotic, an NSAID, and a bone resorption inhibitor. Each possibility represents a separate embodiment of the present invention.

In another embodiment, the process of creating an implant from a composition of the present invention comprises the steps of (a) creating a matrix composition according to a method of the present invention in the form of a bulk material; (b) transferring the bulk material into a mold or solid receptacle of a desired shaped, (c) freezing the bulk material; and (d) lyophilizing the bulk material.

In another embodiment, the present invention provides a pharmaceutical composition comprising a matrix composition of the present invention and a pharmaceutically acceptable excipient.

In another embodiment, a matrix composition of the present invention is in the form of microspheres, following evaporation of the organic solvents. In another embodiment, the microspheres are homogeneous. In another embodiment, the microspheres are manufactured by a process comprising the step of spray-drying. Each possibility represents a separate embodiment of the present invention.

In another embodiment, the present invention provides microspheres made of a matrix composition of the present invention. In another embodiment, the present invention provides a pharmaceutical composition comprising microspheres of the present invention and a pharmaceutically acceptable excipient. In another embodiment, the pharmaceutical composition is in a parenterally injectable form. In another embodiment, the pharmaceutical composition is in an infusible form. In another embodiment, the excipient is compatible for injection. In another embodiment, the excipient is compatible for infusion. Each possibility represents a separate embodiment of the present invention.

In another embodiment, the particle size of microspheres of the present invention is approximately 500-2000 nm. In another embodiment, the particle size is about 400-2500 nm. In another embodiment, the particle size is about 600-1900 nm. In another embodiment, the particle size is about 700-1800 nm. In another embodiment, the particle size is about 500-1800 nm. In another embodiment, the particle size is about 500-1600 nm. In another embodiment, the particle size is about 600-2000 nm. In another embodiment, the particle size is about 700-2000 nm. In another embodiment, the particles are of any other size suitable for pharmaceutical administration. Each possibility represents a separate embodiment of the present invention.

Therapeutic Methods

In another embodiment, the present invention provides a method of administering an antibiotic to a subject in need thereof, the method comprising the step of administering to the subject a matrix composition of the present invention, thereby administering an antibiotic to a subject in need thereof. In another embodiment, a pharmaceutical composition comprising the matrix composition is administered. In another embodiment, an implant comprising the matrix composition is administered. In another embodiment, an injectable formulation comprising the matrix composition is injected. Each possibility represents a separate embodiment of the present invention.

In another embodiment, the present invention provides a method of administering a non-steroidal anti-inflammatory drug (NSAID) to a subject in need thereof, the method comprising the step of administering to the subject a matrix composition of the present invention, thereby administering an NSAID to a subject in need thereof. In another embodiment, a pharmaceutical composition comprising the matrix composition is administered. In another embodiment, an implant comprising the matrix composition is administered. In another embodiment, an injectable formulation comprising the matrix composition is injected. Each possibility represents a separate embodiment of the present invention.

In another embodiment, the present invention provides a pharmaceutical composition for administering an antibiotic to a subject in need thereof, comprising a matrix composition of the present invention. In another embodiment, the pharmaceutical composition is an implant. In another embodiment, the pharmaceutical composition is an injectable composition. Each possibility represents a separate embodiment of the present invention.

In another embodiment, the present invention provides a pharmaceutical composition for administering an NSAID to a subject in need thereof, comprising a matrix composition of the present invention. In another embodiment, the pharmaceutical composition is an implant. In another embodiment, the pharmaceutical composition is an injectable composition. Each possibility represents a separate embodiment of the present invention.

In another embodiment, the present invention provides a pharmaceutical composition for co-administering an antibiotic and an NSAID to a subject in need thereof, comprising a matrix composition of the present invention. In another embodiment, the pharmaceutical composition is an implant. In another embodiment, the pharmaceutical composition is an injectable composition. Each possibility represents a separate embodiment of the present invention.

In another embodiment, the present invention provides a method of treating periodontitis in a subject in need thereof, said method comprising the step of administering to said subject a matrix composition of the present invention, thereby treating periodontitis. "Periodontitis" refers to an inflammatory diseases affecting the tissues that surround and support the teeth. In another embodiment, periodontitis involves progressive loss of the alveolar bone around the teeth and may eventually lead to the loosening and subsequent loss of teeth if left untreated. Periodontitis in some cases has a bacterial etiology. In another embodiment, the periodontitis is a chronic periodontitis. In another embodiment, the periodontitis is any other type of periodontitis known in the art. Each possibility represents a separate embodiment of the present invention.

In another embodiment, the present invention provides a method of stimulating bone augmentation in a subject in need thereof, said method comprising the step of administering to said subject a matrix composition of the present invention, thereby stimulating bone augmentation. In another embodiment, the subject has a disease or disorder selected from the group consisting of osteosarcoma/malignant fibrous histiocytoma of bone (PDQ), osteosarcoma, chondrosarcoma, Ewing's sarcoma, malignant fibrous histiocytoma, fibrosarcoma and malignant fibrous histiocytoma, giant cell tumor of bone, chordoma, lymphoma, multiple myeloma, osteoarthritis, Paget's disease of bone, arthritis, degenerative changes, osteoporosis, osteogenesis imperfecta, bone spurs, renal osteodystrophy, hyperparathyroidism, osteomyelitis, enchondroma, osteochondroma, osteopetrosis, and a diabetes-associated bone or joint disorder. In another embodiment, the matrix composition is in the form of an implant. Each possibility represents a separate embodiment of the present invention.

In another embodiment, the present invention provides a method of reducing an incidence of complications from orthopedic surgery in a subject in need thereof, said method comprising the step of administering to said subject a matrix composition of the present invention, thereby reducing an incidence of complications from orthopedic surgery. In another embodiment, the orthopedic surgery is selected from the group consisting of hand surgery, shoulder and elbow surgery, total joint reconstruction (arthroplasty), pediatric orthopedics, foot and ankle surgery, spine surgery, knee arthroscopy, knee meniscectomy, shoulder arthroscopy, shoulder decompression, carpal tunnel release, knee chondroplasty, removal of a support implant, knee anterior cruciate ligament reconstruction, knee replacement, repair of femoral neck fracture, repair of trochanteric fracture, debridement of skin, muscle, or bone fracture, repair of knee menisci, hip replacement, shoulder arthroscopy/distal clavicle excision, repair of rotator cuff tendon, repair fracture of radius (bone)/ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture. In another embodiment, the matrix composition is in the form of an implant. In another embodiment, the implant is administered during the orthopedic surgery. Each possibility represents a separate embodiment of the present invention.

In another embodiment, the present invention provides a method of enhancing an effectiveness of surgical regenerative procedure in a subject in need thereof, said method comprising the step of administering to said subject a matrix composition of the present invention, thereby enhancing an effectiveness of surgical regenerative procedure. In another embodiment, the surgical regenerative procedure is a periodontal procedure. In another embodiment, the surgical regenerative procedure comprises administering an implant (an implantology procedure). In another embodiment, the implantology procedure is directed to ridge or sinus augmentation. In another embodiment, the matrix composition is in the form of an implant. In another embodiment, the implant is administered during the surgical procedure. Each possibility represents a separate embodiment of the present invention.

In another embodiment, the present invention provides a method of treating an osteomyelitis in a subject in need thereof, said method comprising the step of administering to said subject a matrix composition of the present invention, thereby treating an osteomyelitis. In another embodiment, the matrix composition is in the form of an implant. In another embodiment, the implant is administered at or near the site of osteomyelitis. Each possibility represents a separate embodiment of the present invention.

In another embodiment, a matrix composition of the present invention is administered for aiding orthopedic bone and soft tissue recovery. The compounds are administered during or after a procedure selected from the group consisting of knee arthroscopy and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of trochanteric fracture, debridement of skin/muscle/bone/fracture, knee arthroscopy repair of both menisci, hip replacement, shoulder arthroscopy/distal clavicle excision, repair of rotator cuff tendon, repair fracture of radius (bone)/ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture.

In another embodiment, a matrix composition of the present invention is administered for homeostasis, reducing infections and avoiding tissue adhesions by the use of products such as sponges and membranes.

In another embodiment, a matrix composition of the present invention is administered for reducing of inflammatory reaction around suture materials.

Methods of Making Matrix Compositions

In order to obtain the compositions of the invention any suitable method may be employed that will yield a homogeneous dispersion of the polymer and the lipids in a water resistant matrix. Advantageously according to some embodiments the methods employed eschew the use of water at any stage of the manufacturing process.

According to some embodiments the polymer is mixed separately with appropriate selected volatile organic solvent(s) on the one hand and the phospholipids together with the active pharmaceutical agent are mixed with its appropriate selected solvent(s) or solvents prior to mixing together with the polymer.

In certain embodiments, the present invention provides a method of producing a matrix composition, the method comprising the steps of:

(a) mixing into a first volatile organic solvent: (i) a biodegradable polyester and (ii) sterol; and (b) mixing separately into a second volatile organic solvent: (i) an active agent; (ii) a phosphatidylcholine and optionally (iii) a phosphatidylethanolamine; and (c) mixing and homogenizing the products resulting from steps (a) and (b).

In another embodiment, phosphatidylethanolamine is included in the volatile organic solvent of step (a) instead of or in addition to a phosphatidylethanolamine added to the volatile organic solvent of step (b). In another embodiment, the biodegradable polyester is selected from the group consisting of PLA, PGA and PLGA. In another embodiment, the biodegradable polyester is any other suitable biodegradable polyester known in the art. In some embodiments the first volatile organic solvent is a non-polar solvent. In some embodiments the second volatile organic solvent is a water miscible solvent. In cases where the active agent is a protein or peptide it is important to select solvents that will not denature or impair the activity of the protein. In particular embodiments the active agent is selected from the group consisting of an NSAID, an antibiotic, an antifungal agent, a steroid, an anticancer agent, an osteogenic factor and a bone resorption inhibitor and mixtures thereof.

In another embodiment, the mixture of step (a) containing a volatile organic solvent is homogenized prior to mixing it with the solution of step (b). In another embodiment, the volatile organic solvent or mixture of volatile organic solvents used in step (a) may be same or different than the volatile organic solvent or mixture of organic solvents used in step (b). In another embodiment, the mixture of step (b) is homogenized prior to mixing it with the mixture of step (a). In another embodiment, the polymer in the mixture of step (a) is lipid saturated. In another embodiment, the matrix composition is lipid saturated. Preferably, the polymer and the phosphatidylcholine are incorporated into the matrix composition. In another embodiment, the active agent as well is incorporated into the matrix composition. In another embodiment, the matrix composition is in the form of a lipid-saturated matrix whose shape and boundaries are determined by the biodegradable polymer. Each possibility represents a separate embodiment of the present invention.

In another embodiment, the phosphatidylethanolamine of methods and compositions of the present invention has saturated fatty acid moieties. In another embodiment, the fatty acid moieties have at least 14 carbon atoms. In another embodiment, the fatty acid moieties have 14-18 carbon atoms. Each possibility represents a separate embodiment of the present invention.

In another embodiment, the phosphatidylcholine of methods and compositions of the present invention has saturated fatty acid moieties. In another embodiment, the fatty acid moieties have at least 14 carbon atoms. In another embodiment, the fatty acid moieties have at least 16 carbon atoms. In another embodiment, the fatty acid moieties have 14-18 carbon atoms. In another embodiment, the fatty acid moieties have 16-18 carbon atoms. Each possibility represents a separate embodiment of the present invention.

In another embodiment, the weight ratio of total lipids to polymer in the first volatile organic solvent is such that the polymer in this mixture is lipid-saturated. In another embodiment for purposes of illustration, in the case wherein the polymer is predominantly 50 KDa PLGA (poly (lactic-co-glycolic acid, 1:1 ratio)), the molar ratio of total lipids to 50 KDa PLGA is typically in the range of 10-50 inclusive. In another embodiment, the molar ratio of total lipids to 50 KDa PLGA is between 10-100 inclusive. In another embodiment, the molar ratio is between 20-200 inclusive. In another embodiment, the molar ratio is between 20-300 inclusive. In another embodiment, the molar ratio is between 30-400 inclusive. Each possibility represents a separate embodiment of the present invention.

Each of the components of the above method and other methods of the present invention is defined in the same manner as the corresponding component of the matrix compositions of the present invention.

In another embodiment, step (a) of the production method further comprises adding to the volatile organic solvent a phosphatidylethanolamine. In another embodiment, the phosphatidylethanolamine is the same phosphatidylethanolamine included in step (b). In another embodiment, the phosphatidylethanolamine is a different phosphatidylethanolamine that may be any other phosphatidylethanolamine known in the art. In another embodiment, the phosphatidylethanolamine is selected from the group consisting of the phosphatidylethanolamine of step (b) and a different phosphatidylethanolamine. Each possibility represents a separate embodiment of the present invention.

In another embodiment, step (a) of the production method further comprises adding to the volatile organic solvent a tocopherol.

In another embodiment, step (b) of the production method further comprises adding to the volatile organic solvent physiologically acceptable buffer salts. Non-limiting examples of physiologically acceptable buffer salts are phosphate buffers. A typical example of a phosphate buffer is 40 parts NaCl, 1 part KCl, 7 parts $Na_2HPO_4.2H_2O$ and 1 part $KH_2PO_4$. In another embodiment, the buffer salt is any other physiologically acceptable buffer salt known in the art. Each possibility represents a separate embodiment of the present invention.

In another embodiment, step (b) of the production method further comprises adding to the volatile organic solvent a phospholipid selected from the group consisting of a phosphatidylserine, a phosphatidylglycerol, a sphingomyelin, and a phosphatidylinositol.

In another embodiment, step (b) of the production method further comprises adding to the volatile organic solvent a sphingolipid. In another embodiment, the sphingolipid is ceramide. In another embodiment, the sphingolipid is a sphingomyelin. In another embodiment, the sphingolipid is any other sphingolipid known in the art. Each possibility represents a separate embodiment of the present invention.

In another embodiment, step (b) of the production method further comprises adding to the water-miscible, volatile organic solvent an omega-6 or omega-9 free fatty acid. In another embodiment, the free fatty acid has 16 or more carbon atoms. Each possibility represents a separate embodiment of the present invention.

In another embodiment, each step of the production method is substantially free of aqueous solution. In another embodiment, each step is substantially free of the presence of water or any aqueous solution. As provided herein, producing matrix compositions of the present invention in a water-free process enables lipid saturation.

Upon mixing, a homogenous mixture is formed, since the polymer is lipid-saturated in the mixture of step (a). In another embodiment, the homogenous mixture takes the form of a homogenous liquid. In another embodiment, upon freeze-drying or spray-drying the mixture, vesicles are formed. Each possibility represents a separate embodiment of the present invention.

In another embodiment, the production method further comprises the step of evaporating the solvent present in the product of step (c). In another embodiment, the evaporation utilizes atomization of the mixture. In another embodiment, the mixture is atomized into dry, heated air. Typically, atomization into heated air evaporates all water immediately, obviating the need for a subsequent drying step. In another embodiment, the mixture is atomized into a water-free solvent. In another embodiment, the evaporation is performed by spray drying. In another embodiment, the evaporation is performed by freeze drying. In another embodiment, the evaporation is performed using liquid nitrogen. In another embodiment, the evaporation is performed using liquid nitrogen that has been pre-mixed with ethanol. In another embodiment, the evaporation is performed using another suitable technique known in the art. Each possibility represents a separate embodiment of the present invention.

In another embodiment, a method of the present invention further comprises the step of vacuum-drying the composition. In another embodiment, the step of vacuum-drying is performed following the step of evaporating. Each possibility represents a separate embodiment of the present invention.

In another embodiment, the method of the present invention further comprises the step of evaporating the organic volatile solvent by heating the product of step (c). The heating is continuing until the solvent is eliminated and in a typical temperature between room temperature to 60° C. In another embodiment a step of vacuum-drying is performed following the step of solvent evaporation. Each possibility represents a separate embodiment of the present invention.

Lipid Saturation and Techniques for Determining Same

"Lipid saturated," as used herein, refers to saturation of the polymer of the matrix composition with phospholipids in combination with any hydrophobic drug and targeting moiety present in the matrix, and any other lipids that may be present. As described herein, matrix compositions of the present invention comprise, in some embodiments, phospholipids other than phosphatidylcholine. In other embodiments, the matrix compositions comprise lipids other than phospholipids. The matrix composition is saturated by whatever lipids are present. "Saturation" refers to a state wherein the matrix contains the maximum amount of lipids of the type utilized that can be incorporated into the matrix. Methods for determining the polymer:lipid ratio to attain lipid saturation and methods of determining the degree of lipid saturation of a matrix are described herein. Each possibility represents a separate embodiment of the present invention.

In another embodiment, the matrix composition of methods and compositions of the present invention is substantially free of water. "Substantially free of water" refers, in another embodiment, to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water, as described herein, enables lipid saturation. Lipid saturation confers upon the matrix composition ability to resist bulk degradation in vivo; thus, the matrix composition exhibits the ability to mediate extended release on a scale of several weeks or months. Each possibility represents a separate embodiment of the present invention.

In another embodiment, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

In another embodiment, the matrix composition is dry. "Dry" refers, in another embodiment, to the absence of detectable amounts of water or organic solvent.

In another embodiment, the water permeability of the matrix composition has been minimized. "Minimizing" the water permeability refers to a process of producing the matrix composition in organic solvents, as described herein, in the presence of an the amount of lipid that has been determined to minimize the permeability to penetration of added water. The amount of lipid required can be determined by hydrating the vesicles with a solution containing tritium-tagged water, as described herein.

In another embodiment, "lipid saturation" refers to filling of internal gaps (free volume) within the lipid matrix as defined by the external border of the polymeric backbone. The gaps are filled with the phospholipids in combination with other type of lipids, hydrophobic drug and targeting moiety present in the matrix, to the extent that additional lipid moieties can no longer be incorporated into the matrix to an appreciable extent.

In one embodiment, the following method is used to determine the degree of lipid saturation:

Following manufacture, vesicles are hydrated and isolated by centrifugation or filtration. Lipids that not entrapped in the vesicles form free micelles or liposomes and are located in the supernatant. The overall lipid contents of the supernatant and the vesicles are quantified. In this manner, the entrapped vs. free lipid contents are determined for various formulation containing different lipid:polymer ratios at the outset. Thus, the actual, experimental, maximum lipid/polymer ratio is determined.

In another embodiment, the following method is used to determine the degree of lipid saturation:

Following manufacture, vesicles are hydrated with a solution containing tritium-tagged water, washed with tritium-free solution, and isolated by centrifugation or filtration, and the amount of water entrapped per polymer mass is quantified. This is repeated with different lipid:polymer ratios, in order to determine the amount of lipids required to saturate the free volume in the polymeric vesicles.

"Zero-order release rate" or "zero order release kinetics" means a constant, linear, continuous, sustained and controlled release rate of the pharmaceutical active agent from the polymer matrix, i.e. the plot of amounts of pharmaceutical active agent released vs. time is linear.

EXPERIMENTAL DETAILS SECTION

Abbreviations used: phosphoethanolamine=PE; phosphatidylcholine=PC; 1,2-dimyristoyl-sn-glycero-3-phosphoethanolamine=DMPE (14:0); 1,2-dipalmitoyl-sn-glycero-3-phosphoethanolamine=DPPE (16:0); 1,2-distearoyl-sn-glycero-3-phosphocholine=DSPC (18:0); 1,2-dipalmitoyl-sn-glycero-3-phosphocholine=DPPC (16:0); 1,2-dioleoyl-sn-glycero-3-phosphocholine=DOPC (18:1); 1-palmitoyl-2-{6-[(7-nitro-2-1,3-benzoxadiazol-4-yl)amino]hexanoyl}-sn-glycero-3-phosphocholine=NBD-PC

Example 1. Platform Technology for Production of Drug Carrier Compositions

Overview

To produce lipid-saturated polymer matrices, two mixtures are created.
1. A biodegradable polymer and a sterol and/or phospholipid component are mixed with a volatile organic solvent, which is mixed to yield a solution or suspension of lipid-saturated polymer matrix, as measured by its differential scanning calorimetric (DSC) profile.
2. The active agent and a phospholipid component are mixed with a second volatile organic solvent to yield a second solution or suspension.
3. The two solutions or suspensions are combined and mixed until equilibrium is reached; the organic solvents are then evaporated, yielding a drug-containing, lipid-saturated polymer matrix.

Exemplary Protocol

I. Preparation of First Solution

Polymer (PLGA, PGA, PLA, or a combination thereof) and a polar lipid such as a sterol (e.g. cholesterol) and/or alpha- or gamma tocopherol and/or phosphatidyl ethanolamine are mixed into a volatile organic solvent (e.g. ethyl acetate with/without chloroform). The mixture is mixed. The entire process is performed typically at room temperature. A first lipid-polymer mixture is thus obtained.

II. Preparation of Second Solution

The following materials are mixed with a volatile organic solvent (typically N-methylpyrrolidone [NMP], methanol, ethyl acetate or combination thereof)
  a. Active compound.
  b. A phosphocholine or phosphatidylcholine derivative, e.g. 1,2-distearoyl-sn-glycero-3-phosphocholine (DSPC) or dioleoyl-phosphatidylcholine (DOPC), present as 30-90 mass % of all lipids in the matrix, i.e. 30-90 mass % of phospholipids, sterols, ceramides, fatty acids etc.
  c. In some experiments a phosphatidylethanolamine e.g. dimethyldimyristoyl phosphatidylethanolamine (DMPE) or dipalmitoyl-phosphatidylethanolamine (DPPE)—present as 0.1-50 mass % of all lipids in the matrix.
  d. In some experiments, a targeting moiety, e.g. a fibronectin-hydrogenated phosphatidylethanolamine (HPE) complex, is included as 0.1-10 mol % of all lipids in the matrix. To form this complex, a fibronectin protein or fragment thereof comprising the collagen-binding domain is bound to the amine head group of HPE by a thioether bond.
  e. In some experiments, 0.1-15 mass % of a free fatty acid, e.g. linoleic acid (LN), or oleic acid (OA), is included as 0.1-10 mass % of all lipids in the matrix.
  f. In some experiments, a salt, such as phosphate salts, is included.

The second mixture is mixed, homogenized or sonicated. In some cases, prior to mixing, homogenization or sonication, a non-polar, volatile organic solvent, e.g. ethyl acetate, is included with the mixture, which is stirred gently for 30 minutes. Typically the entire process is conducted at room temperature, but higher temperatures of up to 45° C. are used, typically when highly saturated lipids are used.

No water is required in the mixture.

III—Mixing the Polymer with the Drug/Protein Mixture

The second suspension (or solution) is added to the first solution under stirring. Stirring is continued for up to 5 h. The entire process is performed at room temperature and up to 60° C., all according to the specific formulation, the nature of the lipids in use and the specific drug. The resulting mixture should be homogenous.

IV—Evaporation of the Solvents

In some experiments, the solution from stage III is atomized into dry, heated air.

In other experiments, the solution from stage III is atomized into ethanol covered by liquid nitrogen or only liquid nitrogen without ethanol, after which the nitrogen and/or ethanol (as above) are evaporated.

In other experiments, when coating of surfaces is performed, the suspension from stage III is mixed with the particles or devices to be coated followed by evaporation of the volatile organic solvents. The entire coating process is performed at a temperature of 30-60° C.

V—Vacuum Drying

Coated particles and coated devices are vacuum-dried for storage.

Example 2. Preparation of Doxycycline Hyclate—Bone Particles Filler Formulation for Treatment of Bone Infection (Osteomyelitis or Filling of Bone Effects Caused by Trauma)

I. Preparation of First Solution

The following materials are mixed into ethyl acetate:
  50-75 KDa PLGA (poly (lactic-co-glycolic acid, 85:15 ratio))
  Cholesterol-50%-100% w/w vs. PLGA.

The mixture is mixed. The entire process is performed at room temperature. A fat-polymer combination matrix is thus obtained.

II. Preparation of Second Solution

The following materials are mixed with a volatile organic solvent (methanol and ethyl acetate)
  a. Active compound, —an antibiotic Doxycycline hyclate
  b. A phosphatidylcholine, —1,2-distearoyl-sn-glycero-3-phosphocholine (DSPC) present as 300-700% w/w vs. PLGA.

The mixture is mixed well. The entire process is conducted at room temperature. When phosphatidylcholine having long saturated fatty chains is used (e.g. DSPC) the process is typically performed at higher temperatures of about 40-50° C.

No water is required in the mixture.

III—Mixing the Polymer with the Drug Mixture

The second solution or suspension is added to the first suspension, typically under stirring. Stirring is continued for 1-5 minutes. The entire process is performed at a temperature of 20-50° C. depending of the lipid used.

IV—Evaporation Following Surface Coating

In order to coat bone filler particles, the particles are added to the mixture of stage III followed by evaporation of the volatile organic solvents. The entire process is performed at a temperature of 40-50° C.

The ratio between the volume and the percentage of solids in the mixture of stage III and the mass of the bone particles will determine the release period of the drug post hydration of the coated particles.

V—Vacuum Drying

Coated bone particles are vacuum-dried for storage.

Figure 1B:
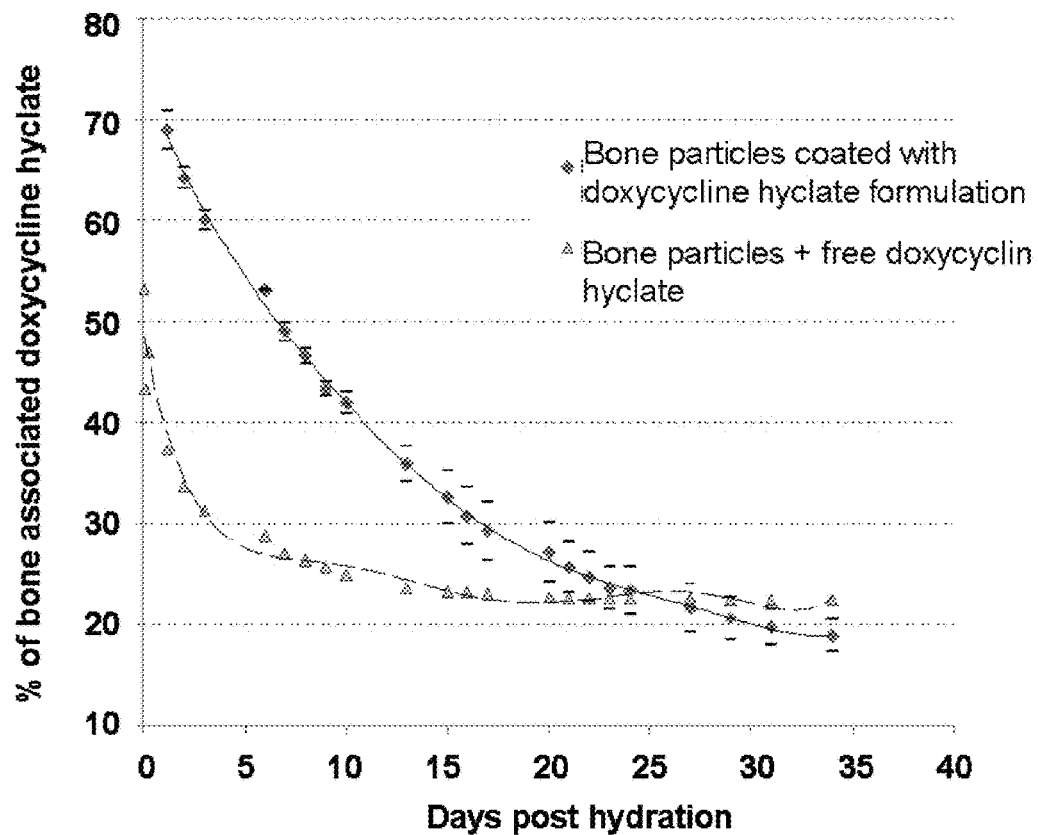
Figure 2:
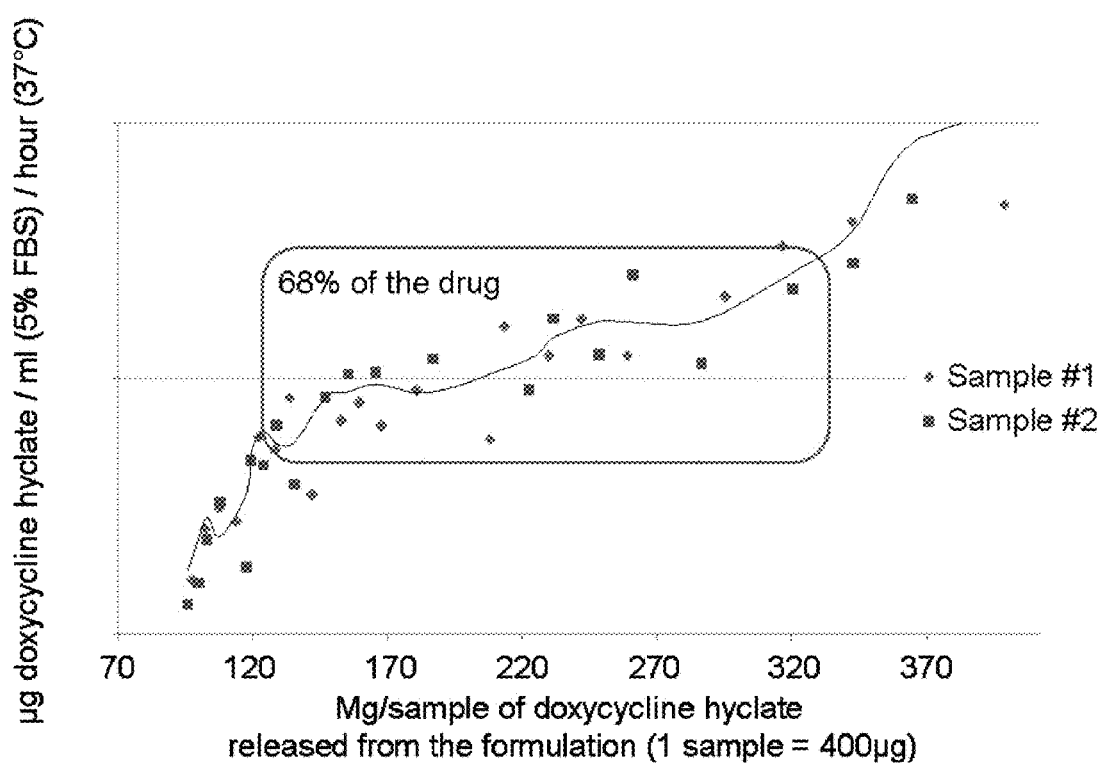
FIG. 2: The majority (~70%) of DOX encapsulated in the formulation of the present invention is being released following zero order kinetics. Y axis represents the velocity of the release of DOX in µg/ml/hour.

The ability of bone filler particles (xenografts bovine-commercial-BioOss®) coated with the matrix composition of the present invention to sustained release the drug (doxycycline hyclate) is shown in FIGS. 1 and 2. The rate of sustained release of Doxycycline hyclate encapsulated within the matrix composition of the present invention was measured and compared to the release rate of the drug from bone particles socked with free DOX solution (having the same amount of DOX). It was found that the drug was released constantly for about three weeks (FIGS. 1 A and B) following zero order kinetics (FIG. 2). The velocity values displayed in FIG. 2 were calculated following the assumption that the coated bone particles constitute only 200/% of the total amount of bone particles used as bone fillers and the drug once released, diffuses to the free volume between the bone particles.

Figure 3A:
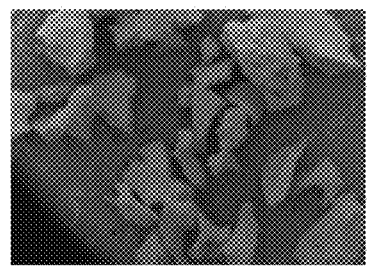
FIGS. 3A, 3B and 3C: The macro-structure of the bone particles is not affected by coating with the formulation of the present invention. (A) the original structure of bone particles; (B) bone particles coated with the formulation of the present invention encapsulating DOX; (C) the bone particles of (B) after 60 days of incubation in serum.
Figure 3B:
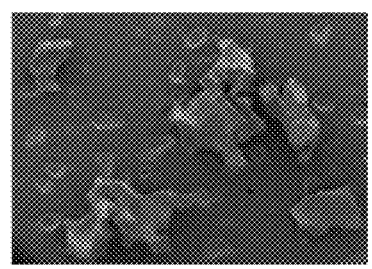
Figure 3C:
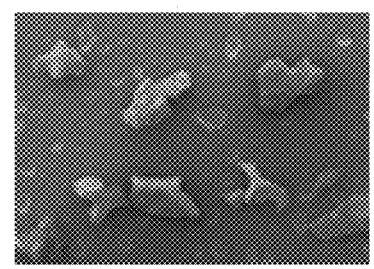

The macro-structure of the bone particles before (FIG. 3A) and after coating with the matrix composition of the present invention (FIGS. 3B and 3C) was studied. As can be seen in FIG. 3, the structure of the bone particles is not affected by coating; furthermore, the macro-structure of the bone particles is maintained even after 60 days of incubation in serum.

Figure 4A:
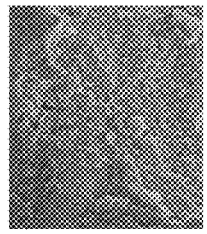
FIGS. 4A, 4B, 4C, 4D and 4E: The matrix formulation coating the surface of bone particles undergoes gradual surface degradation. (A) untreated surface; (B) surface of a coated bone particle; (C) the surface of a coated bone particle after 1 day in 10% FBS at 37° C.; (D) the surface of coated bone particle after 30 days in 10% FBS at 37° C.; (E) surface of coated bone particle after 60 days in 10% FBS at 37° C.
Figure 4B:
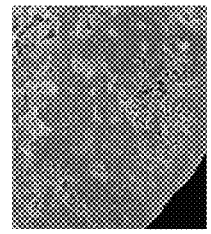
Figure 4C:
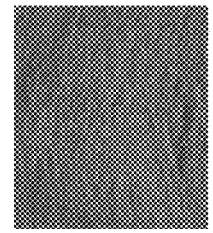
Figure 4D:
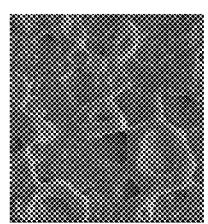
Figure 4E:
Figure 5:
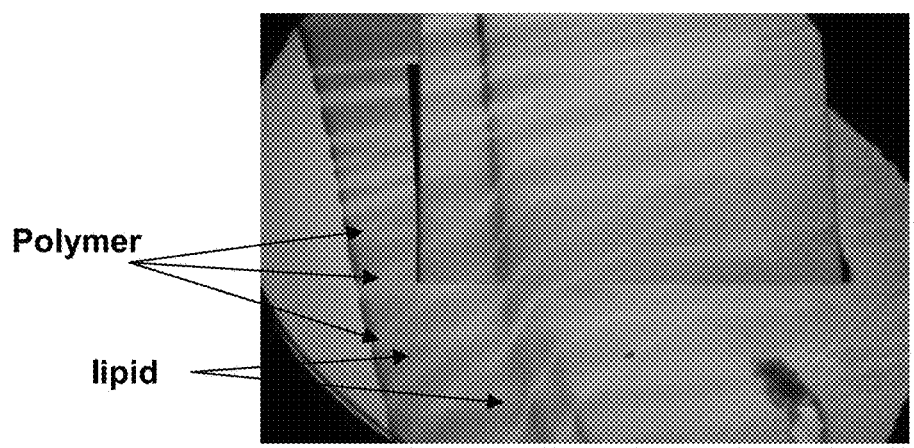
FIG. 5: The ordered structured of the matrix formulation (PLGA (85:15), DPPC (16:0), Cholesterol 10%) is demonstrated by electron microscopy (×18,000). The bright colored lines represent the polymer, where as the lipid is represented by the dark filling in between the polymeric material.

The structure of bone particles surfaces before (FIG. 4A) and after coating with the matrix composition of the present invention (FIG. 4B-E) was studied by SEM. The matrix composition contained DSPC, PLGA (85:15), cholesterol and the antibiotic doxycycline hyclate. The coated bone particles were incubated in 10% FBS at 37° C. for 2 months. As can be seen the coating is homogenous and opaque, furthermore it covers most of the bone surface. With time, the coating is eliminated gradually, layer by layer by surface corrosion, during which the drug is being released. It can be further seen in FIG. 4E that after 60 days of incubation the coating is almost completely eliminated, leaving the bone surface as in its original, uncoated form. The ordered structure of the matrix composition of the invention is shown in FIG. 5. Coated bone particles (PLGA (85:15), DPPC (16:0) and Cholesterol 10%), were analyzed by electronic microscopy (×18,000) and negative staining (data not shown). The bright colored lines represent the polymer, where as the lipid is represented by the dark filling in between the polymeric material.

Figure 6:
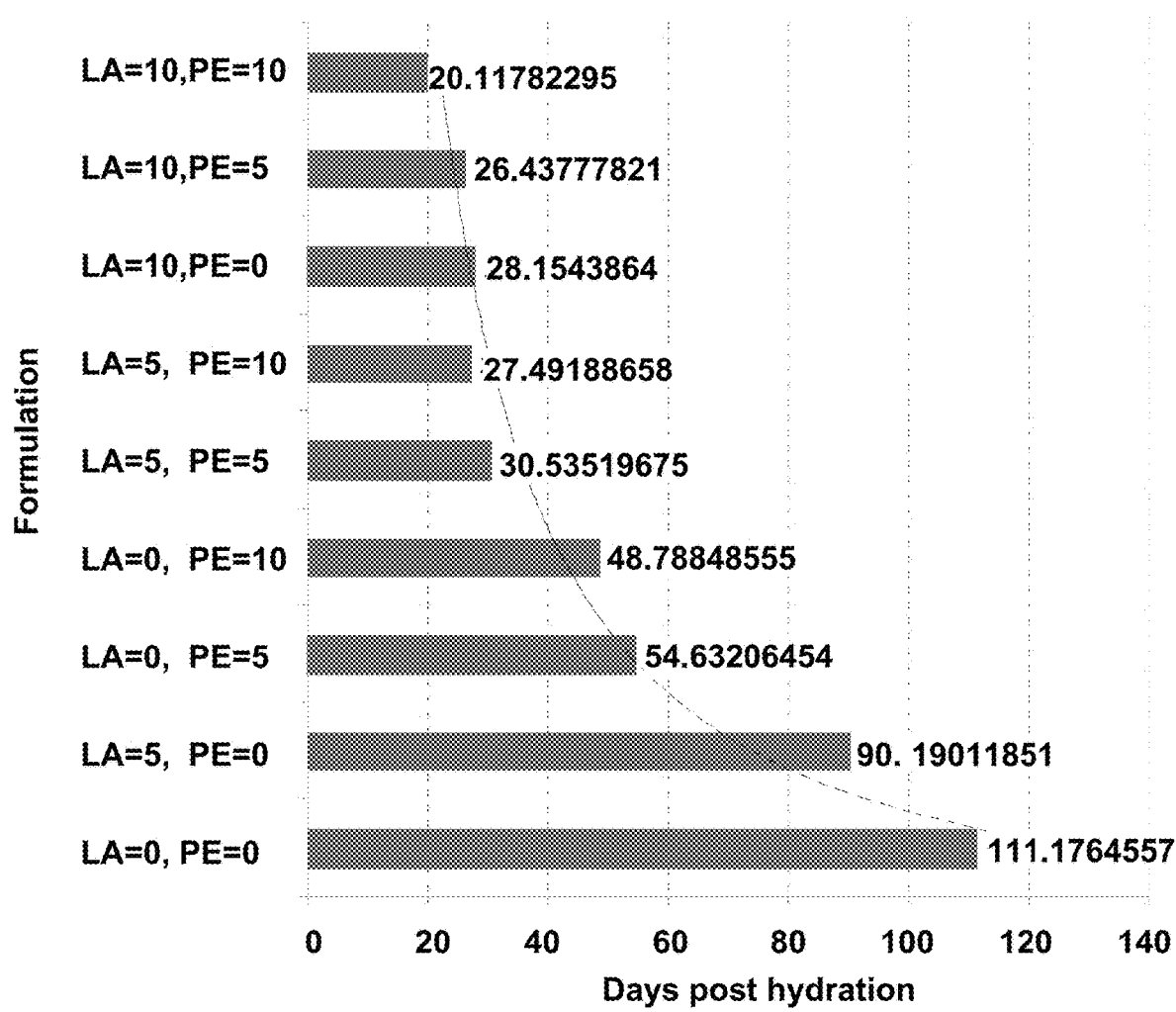
FIG. 6: The specific polymer/lipid compositions of the formulations of the present invention determine the release rate of a given drug. The influence of various concentrations of lauric acid (LA) and phosphatidylethanolamine (PE) given in w/w % of the formulation on the release period of 90% of the entrapped drug.
Figure 7:
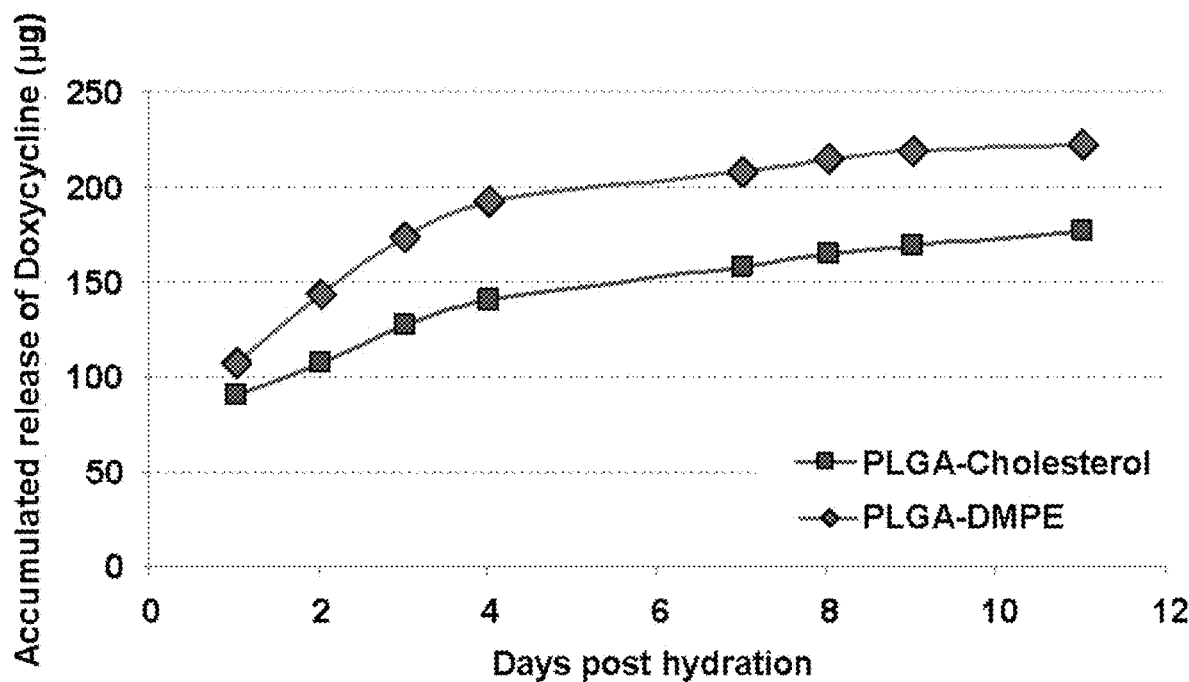
FIG. 7: The use of dimethyl phosphatidylethanolamine (DMPE) vs. cholesterol in formulations of the present invention. Comparison of the release profile of DOX from bone particles coated with a formulation that comprises dimethyl dimyristoyl phosphatidylethanolamine (DMPE) (diamonds) in the first organic solution during preparation versus a formulation that comprises cholesterol (squares) at the same preparation stage following hydration of the bone particles (5% serum at 37° C.).

The influence of different polymer/lipid compositions on the release rate of a given drug was measured using fluorescein entrapped within a matrix compositing PLGA (75:25), DPPC as the main phospholipid and varying amounts of lauric acid (LA) and phosphatidylethanolamine (PE) having saturated fatty acid moieties of at least 14 carbons. As can be seen in FIG. 6 the expected release period of 90% of the entrapped molecule was dramatically influenced by the LA:PE content. The release lasted between about 20 to about 110 days when LA:PE w/w % ratio was varied between 10:10 to 0:0 respectively (vs. the total mass of the formulation). The drug release profile from bone particles coated with matrix formulation comprising PE versus bone particles coated with matrix formulation comprising cholesterol was compared. FIG. 7 demonstrates that the release profiles of DOX from coated bone particles comprising PE or cholesterol behaves similarly.

Figure 8:
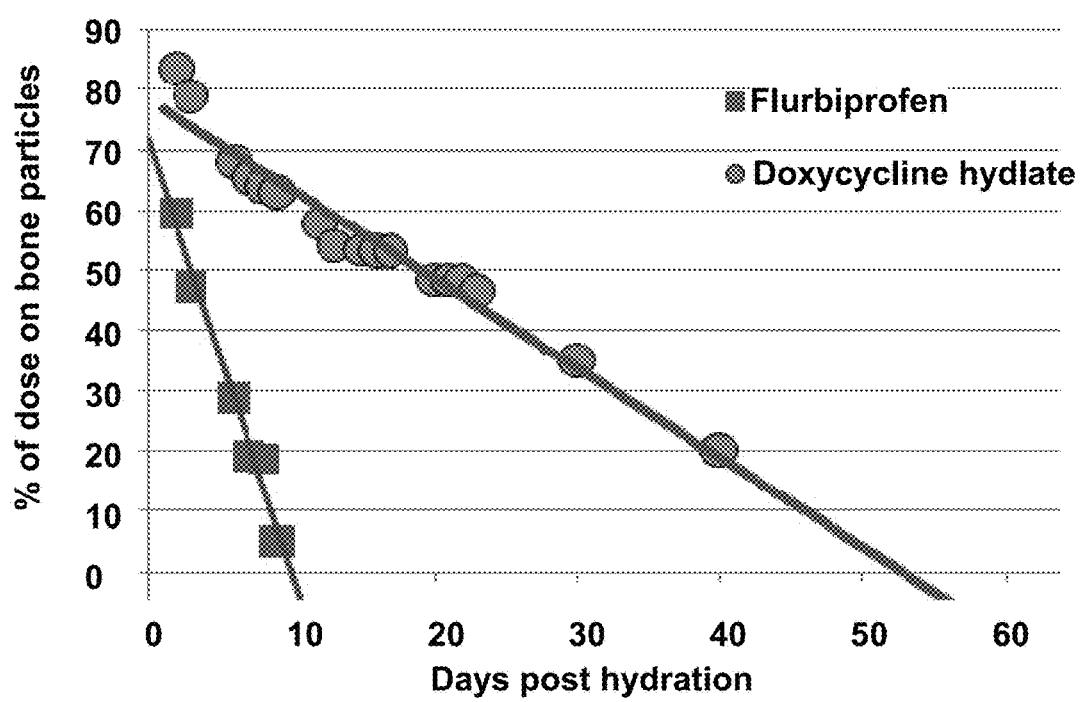
FIG. 8: The nature of the polymer and phospholipid determines the release rate of the entrapped pharmaceutical active agent. Flurbiprofen is released from a matrix comprising PLGA (50:50) and DMPC (14:0), whereas doxycycline hyclate is released from a matrix composition comprising PLGA (85:15) and DSPC (18:0).

The fact that different polymer/lipid compositions influence the release rate can be used to fulfill different clinical needs. For example, anti inflammation treatment with NSAID is commonly a short term treatment (e.g. few days) thus by using a fast degrading polymer such as PLGA 50:50 and a 14:0 phospholipid such as DMPC, full release of the drug can be completed within 10 days as can be seen in FIG. 8. In contrast, when the antibiotic drug, DOX, was associated with a slow degrading polymer such as PLGA 85:15 and a 18:0 phospholipid such as DSPC, complete release of the drug was accomplished after more than 50 days (FIG. 8).

Figure 9:
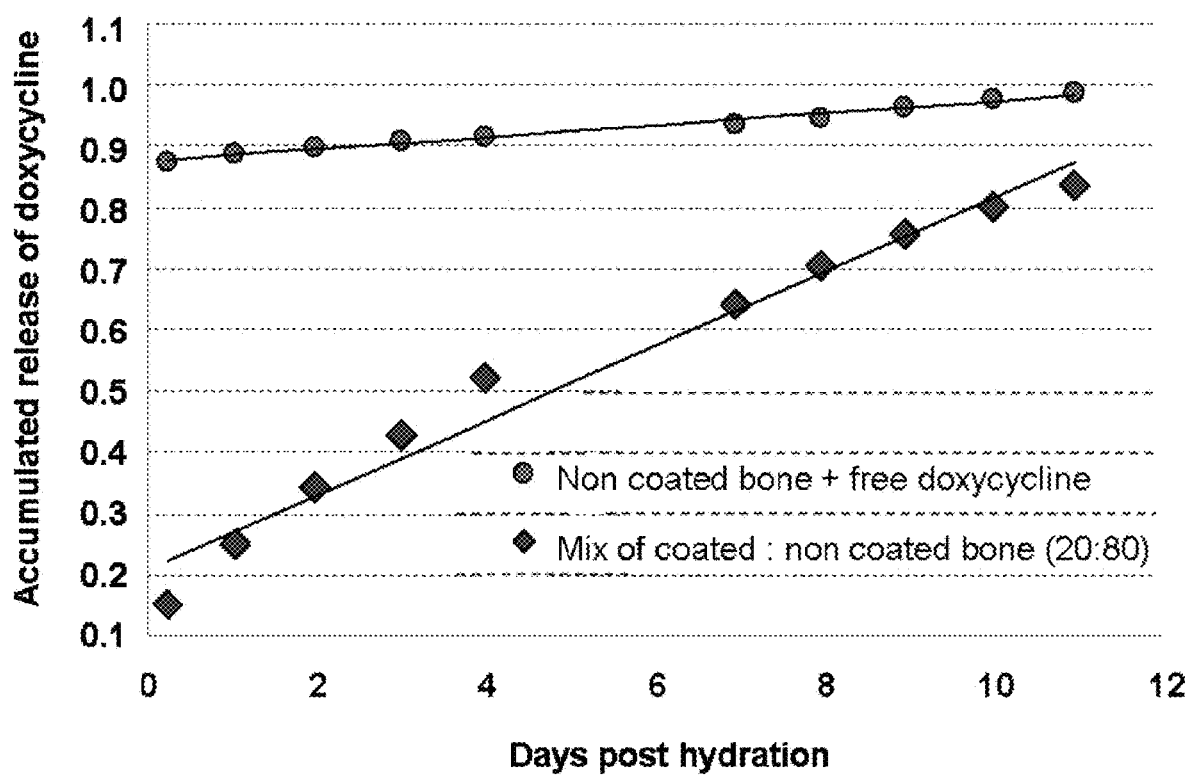
FIG. 9: The release profile of DOX from bone particles coated with a formulation that contains DOX and mixed with similar not-coated bone particles in a ratio of 1:4 (diamonds) versus the release profile of free DOX mixed with the same amount of not-coated bone particles following bone particles hydration (5% serum at 37° C.).

The release profile of DOX from a mixture of coated and non coated bone (xenografts bovine—commercial—BioOss) particles was measured. The coated particles were mixed with similar plain (not-coated) bone particles in a ratio of 1:4. As control we followed the release of a similar dose of free DOX from plain (not-coated) bone particles soaked with the free drug. As can be seen in FIG. 9, following hydration (5% serum at 37° C.) the release of DOX from the formulation was not affected by the presence of the non-coated particles. In comparison, most of the drug from the uncoated bone particles soaked with DOX was released shortly after hydration (88% in 3 hours as compared to about 15% of the drug released from the coated bone particles during the same period). The formulation in this study comprised PLGA 75:25 and DPPC.

Figure 10:
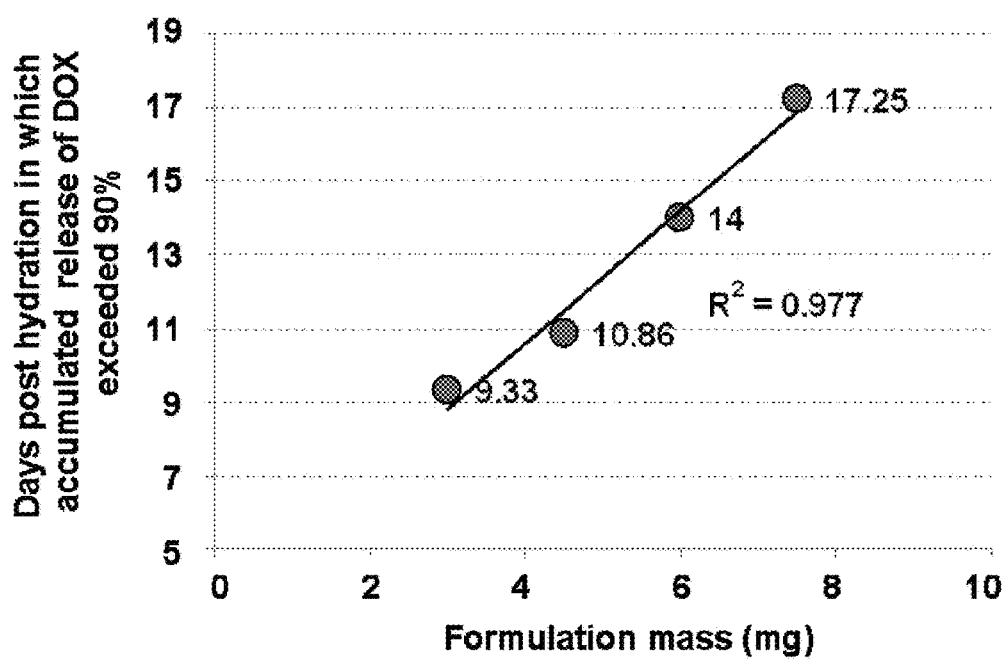
FIG. 10: The duration of drug release from bone particles coated with the formulations of the invention is linearly depended on the formulation mass. Bone particles (12 mg/sample) were coated with different mass of formulation containing DOX (X-axis reflecting the formulation mass in mg). Following bone particles hydration, the release of DOX from the formulation was monitored. Y-axis is reflecting the day in which the accumulated release of the entrapped DOX exceeded 90% of the overall entrapped dose.

We have further demonstrated that the duration of drug release from coated bone particles is linearly depended on the formulation mass. The release of DOX from bone particles (12 mg/sample) coated with different mass of the DOX containing matrix formulation was compared. Following hydration (5% serum at 37° C.) the duration of release of 90% of the initial DOX amount in the formulation was monitored (FIG. 10). The linear dependence between the duration of drug release and the mass of the coating matrix formulation suggests that the drug is released by gradual degradation of the matrix, and the release rate is not affected by the overall mass of the formulation.

Example 3: Preparation of 1,3-Thiabendazole (TBZ) Formulation

Stock Solutions:

a. PLGA/ethyl acetate, 300 mg/ml (SS1, 1 ml): (i) Weight 300 mg PLGA (50:50; Sigma) into 4 ml glass vile, (ii) add 1 ml ethyl acetate, (iii) vortex for 5 minutes, (iv) Stir for 12-18 hours at room temperature (RT), (v) confirm that the polymer grains are totally dissolved, (vi) close under $N_2$, wrap with aluminum foil and keep it at RT, (vii) the solution is good for 1 month.

b. Cholesterol/ethyl acetate, 30 mg/ml (SS2, 1 ml): (i) Weight 30 mg cholesterol (Sigma 99%) into 4 ml glass vile, (ii) add 1 ml of ethyl acetate, (iii) vortex for 5 minutes at RT, (iv) confirm that the cholesterol is totally dissolved. Otherwise, continue to vortex for more 2 minutes, (v) close under $N_2$, wrap with aluminum foil and keep it at RT, (vi) the solution is good for 1 month.

c. Ethyl acetate: Methanol 1:1 (SS2.1): (i) Put 10 ml of Ethyl acetate into a 20 ml glass vile, (ii) add 10 ml methanol into the same vile, (iii) vortex for 20 seconds, (iv) keep the solution at RT, (v) the Solution is good for 1 month.

d. Thiabendazole (TBZ)/ethyl acetate: methanol 1:1, 10 mg/ml (SS3, 1 ml): (i) weight 10 mg TBZ into 4 ml glass vile, (ii) add 1 ml of SS2.1 stock solution, (iii) vortex for 5 minutes at RT, (iv) confirm that TBZ is totally dissolved. Otherwise, continue to vortex for more 2 minutes. The solution has some white turbidity, (v) close under N₂, wrap with aluminum foil and keep it at RT, (vi) the solution is good for 1 month.

Solution A (1.2 ml):
  i. Add 1 ml SS2 (CH-EA, 30 mg CH) to 0.2 ml SS1 (PLGA/EA, 60 mg PLGA) into 4 ml glass vile.
  ii. Vortex for 5 minutes at RT.
  iii. Confirm that the mixture is uniform and lucid. Otherwise go back to ii.
  iv. Close under N₂, wrap with aluminum foil and keep it at RT.
  v. The solution is good for 1 month.
  vi. Concentrations solution A: [CH]=25 mg/ml; [PLGA]=50 mg/ml.

Solution B (1 ml):
  i. Weight 225 mg phospholipids (14:0) into 4 ml glass vile.
  ii. Add 0.75 ml SS3 (TBZ/EA-MET, 7.5 mg TBZ).
  iii. Add 0.25 ml ethyl acetate into the vile.
  iv. Vortex for 2 minutes at RT.
  v. Close under N2, wrap with aluminum foil and keep it at RT.
  vi. The solution is good for 1 month.
  vii. Concentrations: [phospholipid (14:0)]=225 mg/ml, [TBZ]=7.5 mg/ml.

Solution C (1 ml):
  i. Pour 0.4 ml of solution B into a 4 ml glass vile.
  ii. Add 0.6 ml of solution A into the vile.
  iii. Vortex for 2 minutes at RT.
  iv. Check: The solution is liquid at RT, has a pale yellow color with some turbidity.
  v. Close under N₂ and wrap with aluminum foil.
  vi. Concentrations: [CH]=15 mg/ml; [PLGA]=30 mg/ml; [14:0]=90 mg/ml; [TBZ]=3 mg/ml.

Bone Coated Preparation:
  i. Weight 12.5 (±0.5) mg bone particles (Bio-Oss or EndoBon) into 1.8 ml glass vile;
  ii. Wash the bones with purified water (½ ml DDW); pump out the water with the micropipette, followed by vacuum for 12-18 hours.
  iii. Prepare a heating block, heated to 45° C.
  iv. Heat solution C to 45° C. for 30 seconds. Make sure that the solution totally melts and becomes uniform.
  v. Add 50 µl of solution C to the bone particles with a 10-100 µl micropipette.
  vi. Put the 1.8 ml vials, unsealed, in the heating block (45° C.) for 30 minutes.
  vii. Remove from heating and close with a stopper.
  viii. vaccum the (half-sealed) vials with a rotation pump (1×10−1 Torr) for 12-18 hours.
  ix. Separate gently the fused bone particles with a spatula.
  x. Transfer the dry coated bone particles into a new 4 ml glass vile;
  xi. Close under N₂, wrap with aluminum foil and keep it at RT.
  xii. The coated bone particles are good for 1 month.

Figure 11:
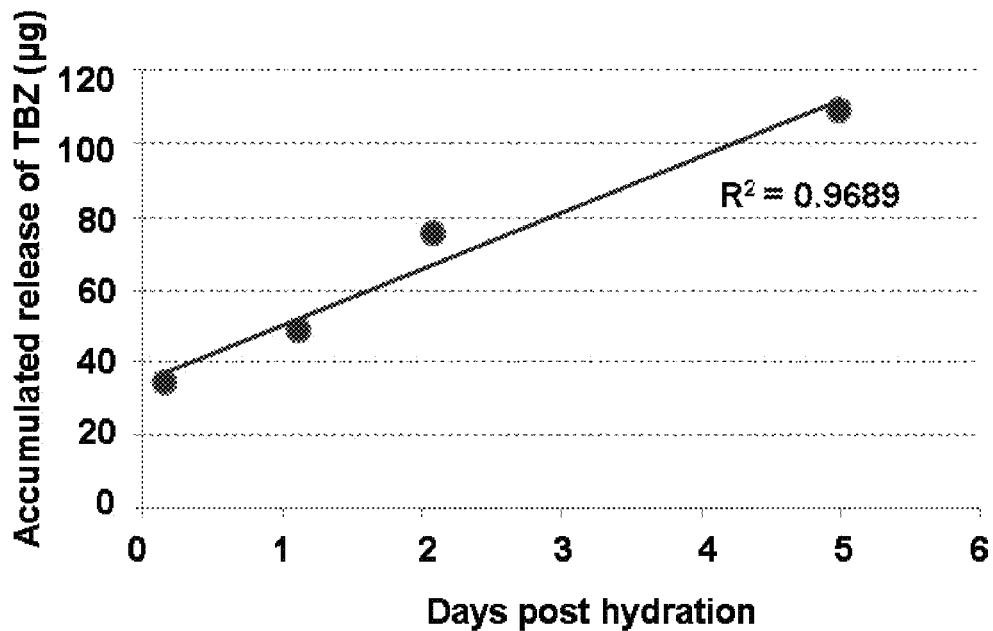
FIG. 11: The release profile of the antifungal drug, Thiobendazole (TBZ), from bone particles coated with a formulation (PLGA 50:50, cholesterol and DMPC (14:0) that contains TBZ (10% of the total mass of the formulation).

The release profile of TBZ from bone particles coated with the TBZ containing matrix composition after hydration (5% serum, 37° C.) can be seen in FIG. 11.

Figure 12:
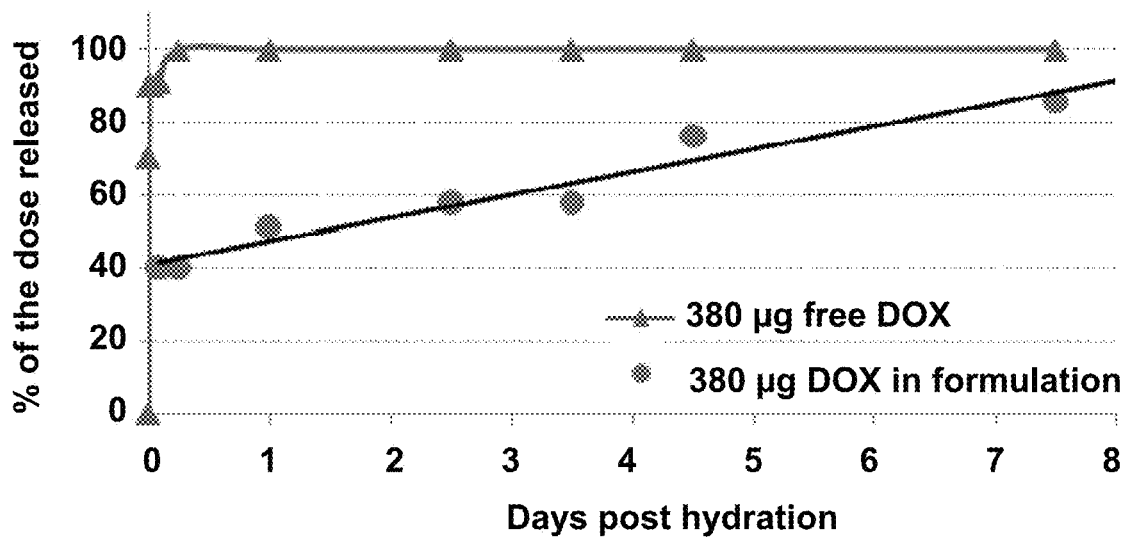
FIG. 12: Antibiotic release from an absorbable gelatin sponge (Gelatamp. ROEKO) coated with the matrix formulation of the invention (PLGA 75:25, PC 16:0, cholesterol 10% and DOX 10%). The release of DOX from an absorbable gelatin sponge pre-wetted with DOX solution having a similar drug dose served as control.

Example 4: Drug Release from Absorbable Gelatin Sponge Containing the Sustained Release Formulation of the Invention A solution containing PLGA—75:25, PC 16:0, cholesterol 10% and Doxycycline hyclate (DOX) 10% was injected into the center of the absorbable gelatin sponge foam cube (Gelatamp. ROEKO). The overall content of DOX in the injected formulation was 380 µg in 25 µl. The solvent was evaporated in a 37° C. incubator and subsequently over night under vacuum. As a control, the common use of pre-wetting with a similar dose of DOX (380 µg) solution was injected into the gelatin sponge tube. Following hydration (5% serum at 37° C.) the release of DOX from the gelatin sponge cube into the surrounding was detected and quantified by HPLC. As can be seen in FIG. 12, while in the control sample, the total amount of DOX was released immediately into the medium, only about 40% of the DOX associated with the PLGA/PC/cholesterol formulation was released into the medium immediately after hydration, while the rest of the drug was gradually released for more than 7 days.

Example 5: SEM Elements Analysis of Coated Bone Particles

Bone particles coated with a matrix formulation (PLGA 50:50, cholesterol and DPPC 16:0) and non coated bone particles were analyzed by SEM element analysis. The element analysis of bone particle surface, coated and non-coated are summarized in the tables 1 and 2 below:

TABLE 1

| non coated bone particle surface. | | |
|---|---|---|
| Element | Wt % | At % |
| CK | 10.05 | 16.91 |
| NK | 02.27 | 03.28 |
| OK | 43.97 | 55.55 |
| NaK | 00.67 | 00.59 |
| MgK | 00.76 | 00.63 |
| PK | 11.59 | 07.57 |
| CaK | 30.68 | 15.47 |
| Matrix | Correction | ZAF |

TABLE 2

| coated bone particle surface. | | |
|---|---|---|
| Element | Wt % | At % |
| CK | 42.28 | 55.73 |
| NK | 02.96 | 03.34 |
| OK | 30.90 | 30.57 |
| NaK | 00.46 | 00.32 |
| MgK | 00.39 | 00.25 |
| PK | 5.94 | 03.04 |
| CaK | 17.08 | 06.75 |
| Matrix | Correction | ZAF |

The element analysis shows that carbon (CK in tables 1 and 2) is the dominant element in bone particles coated with the formulation of the invention. Carbon is the major element in both the polymer used in the formulation (PLGA 50:50) and the lipid used (DPPC 16:0). In contrast, the contents of calcium and phosphate which are dominant elements of the plain bone particles (uncoated bone particles) are at least two times lower on the surface of the coated bone particles.

Figure 13:
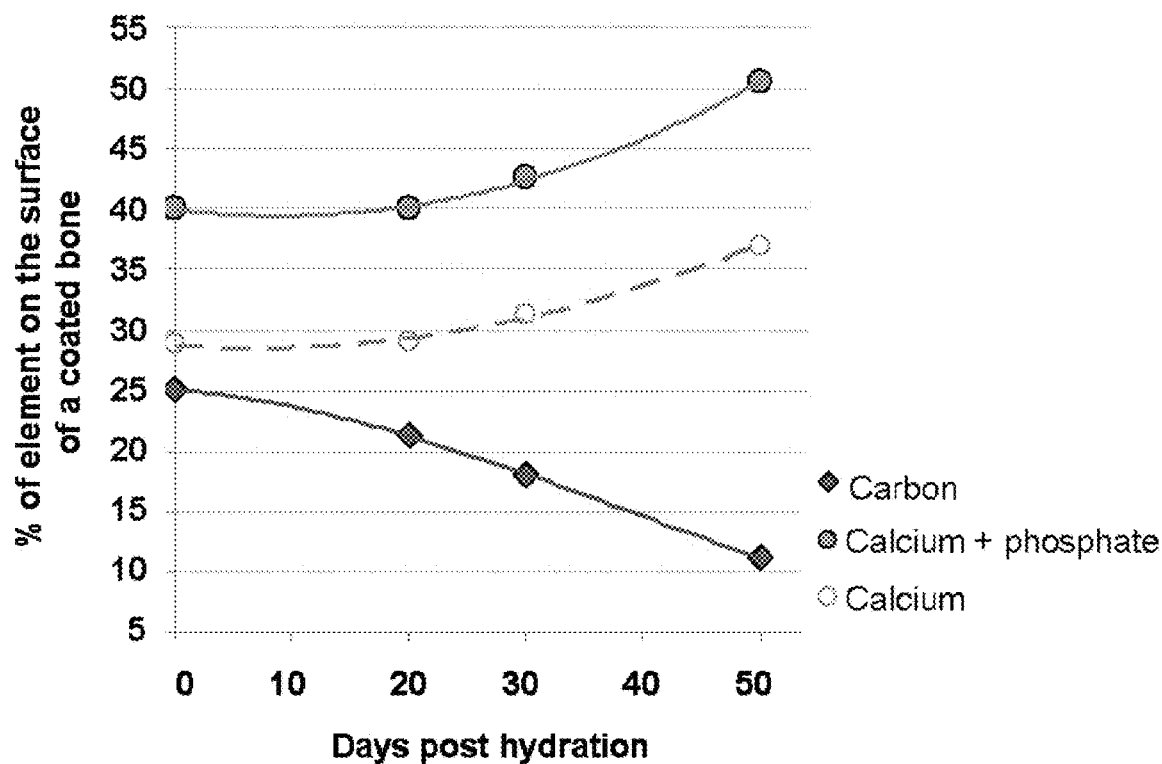
FIG. 13: The degradation of the bone particle coating formulation as reflected by surface element analysis. Following hydration of the coated bone particles, the percentages of carbon, calcium and phosphate atoms on the surface of the coated bone particles were monitored by SEM. The X-axis is presenting the time post hydration of the coated bone samples.

The gradual degradation of the bone particle coating formulation of the present invention after hydration was studied by SEM element analysis. The weight percentages of carbon, calcium and phosphate atoms on the surface of the coated bone particles were monitored by SEM. As can be seen in FIG. 13, following hydration of the coated bone particles the percentage of the carbon atoms on the surface of the coated bone particles decreases with time, whereas the percentages of calcium and phosphate increase with time. These results demonstrate that upon gradual degradation of the coating formulation the surface of the bone particles is gradually exposed.

Example 6: Elevated Turbidity in the Supernatant of Bone Particles Coated with Formulations of the Invention is Correlated with the Appearance of Vesicles in the Supernatant Bone particles (TCP artificial bone substitute—commercial) coated with a formulation of the present invention comprising doxycycline hyclate—DOX) were hydrated in 5% serum at 37° C. After 1 hour the bone particles were separated from the supernatant and the supernatant was analyzed by monitoring its absorbance at 520 nm. The bone particles were re-incubated in a fresh 5% of serum at 37° C. for another 23 hours. After 23 hours the bone particles were separated from the supernatant and the later was analyzed as described before.

Figure 14:
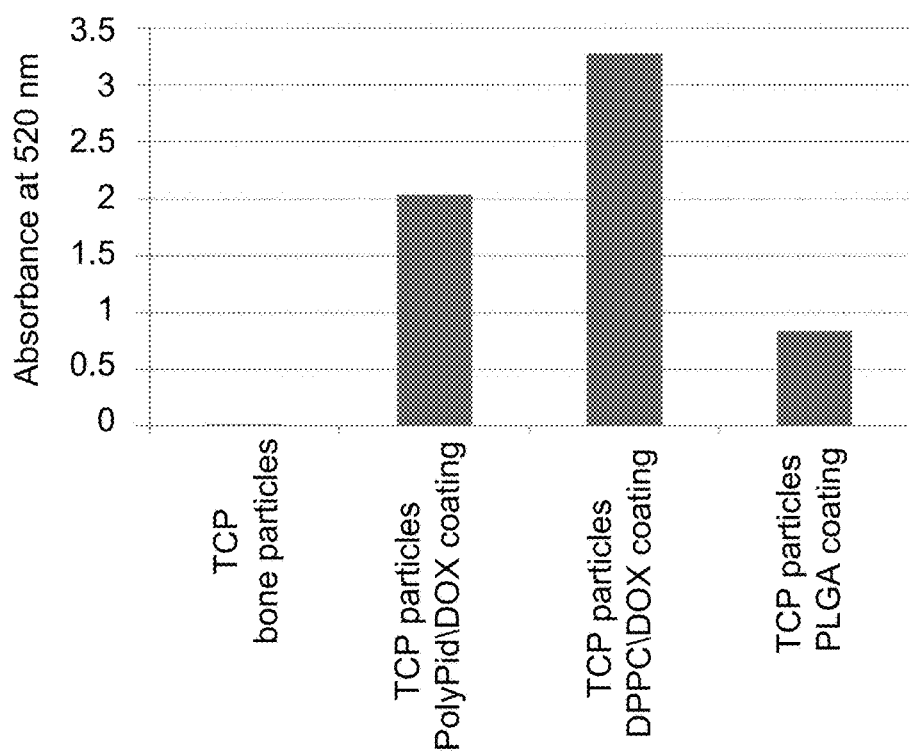
FIGS. 14A, 14B, 14C, 14D and 14E: Turbidity analysis of the supernatant solution (5% serum) of hydrated bone particles: 4 different types of bone particles were analyzed: (i) plain, non-coated bone particles (ii) bone particles coated with the matrix composition of the invention having DOX as the pharmaceutically active agent (iii) bone particles coated with DPPC and DOX and (iv) bone particles coated with PLGA. The turbidities of the supernatants into which the bone particles were immersed were measured 1 hour after hydration and at 37° C. (A). After an hour of incubation the hydration medium was replaced by a fresh medium and turbidity was measured after 23 hours of incubation at 37° C. (B). An electron microscopy image of the hydration solution into which bone particles coated with the matrix formulation of the invention were immersed, taken 24 hours after hydration at 37° C. (C). Size distribution (D) and zeta potential (E) analysis of the material released from hydrated bone particles.
Figure 14:
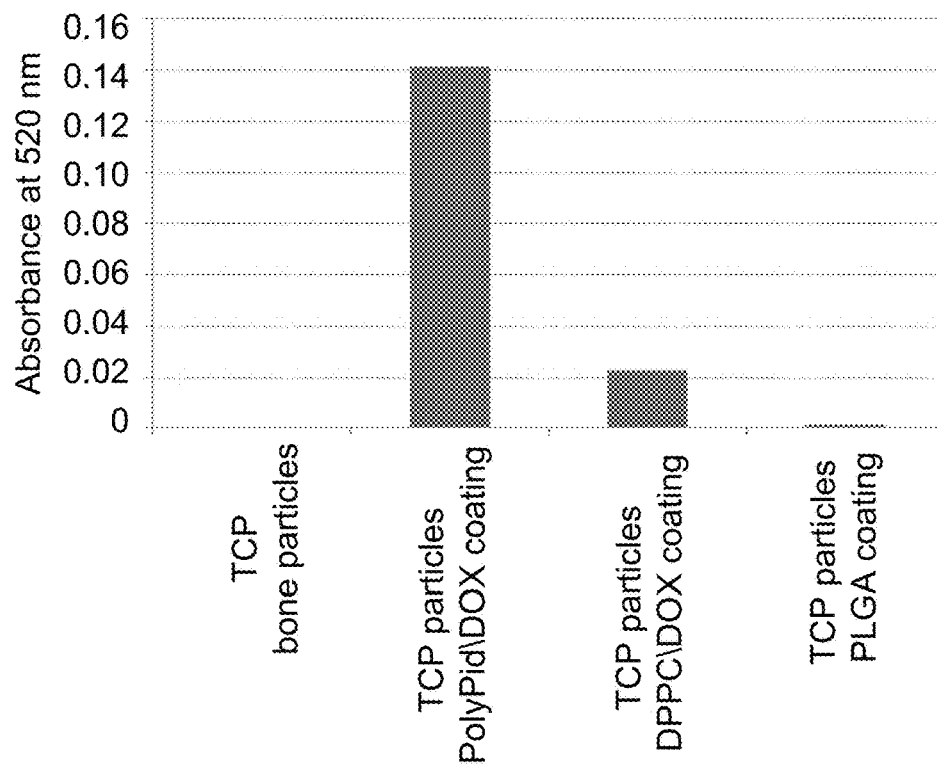
Figure 14:
Figure 14:
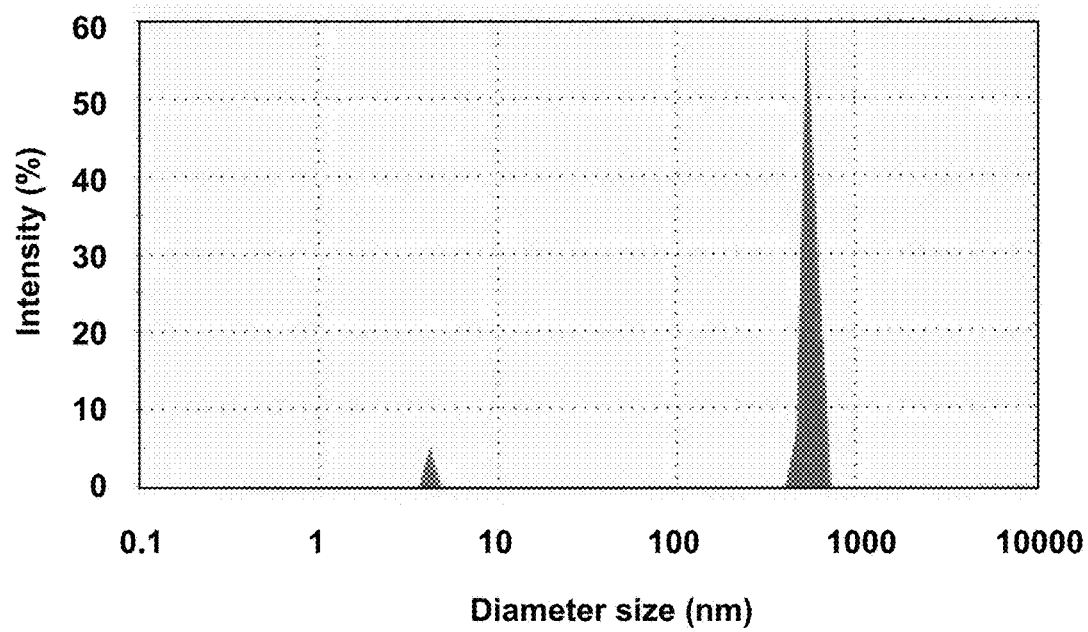

Results:

The supernatant collected from plain uncoated bone particles did not have significant turbidity. In contrast, after 1 h of hydration a significant turbidity was evidenced in supernatants of coated bone particles. Three types of bone particles coatings were tested: (i) the formulation of the present invention comprising an antibiotic agent and (ii) DPPC and an antibiotic agent coating and (iii) PLGA coating. Bone particles that were coated with PLGA showed smaller increase in turbidity ($OD_{520}$ nm~0.85) as compared to the DPPC coated particles ($OD_{520}$ nm>3) or the particles coated with the formulation of the invention ($OD_{520}$ nm~2.0) (FIG. 14A). After additional 23 hours of incubation (hydration) under the same conditions the turbidity was much lower than that measured after 1 h, and evidenced only in bone coating formulations containing lipids (formulations (i) and (ii)) (FIG. 14B).

The supernatant removed from plain non coated bone particles as well as coated bone particles ((i), (ii) and (iii) as described above) after the second round of incubation for 23 hours, were further analyzed by electron microscopy (magnitude of 18,000) and negative staining. In the supernatants taken from bone particles coated with the formulation of the present invention (i) or with DPPC (ii), vesicle like structures of different sizes were evidenced (FIG. 14C).

Figure 14E:
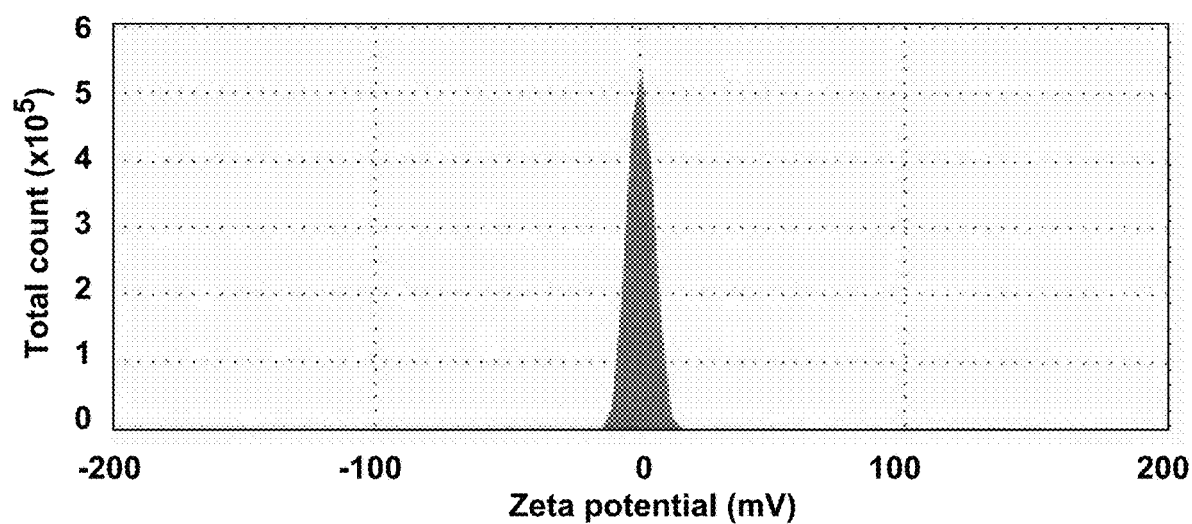

The nature of the released material from bone particles coated with a matrix formulation containing PLGA (85:15), DPPC (16:0) and the antibiotic drug (DOX), was further analyzed by a Size Distributor (Malvern Instruments DST ver. 5). The coated bone particles were hydrated with 5% serum and incubated for 24 hour at 37° C. The supernatant was removed after 24 hours and analyzed. The released material was characterized by two particle populations having an average size of 550.3 nm and 4.2 nm (FIG. 14D). The zeta potential of the particles, measured using the same instrument, was found to be close to zero (0.0225 mV) (FIG. 14E). The diameter size of the released material as well as its neutral charge may suggest that these vesicle like particles are composed mainly from the DPPC found in the coating matrix formulation.

Figure 15:
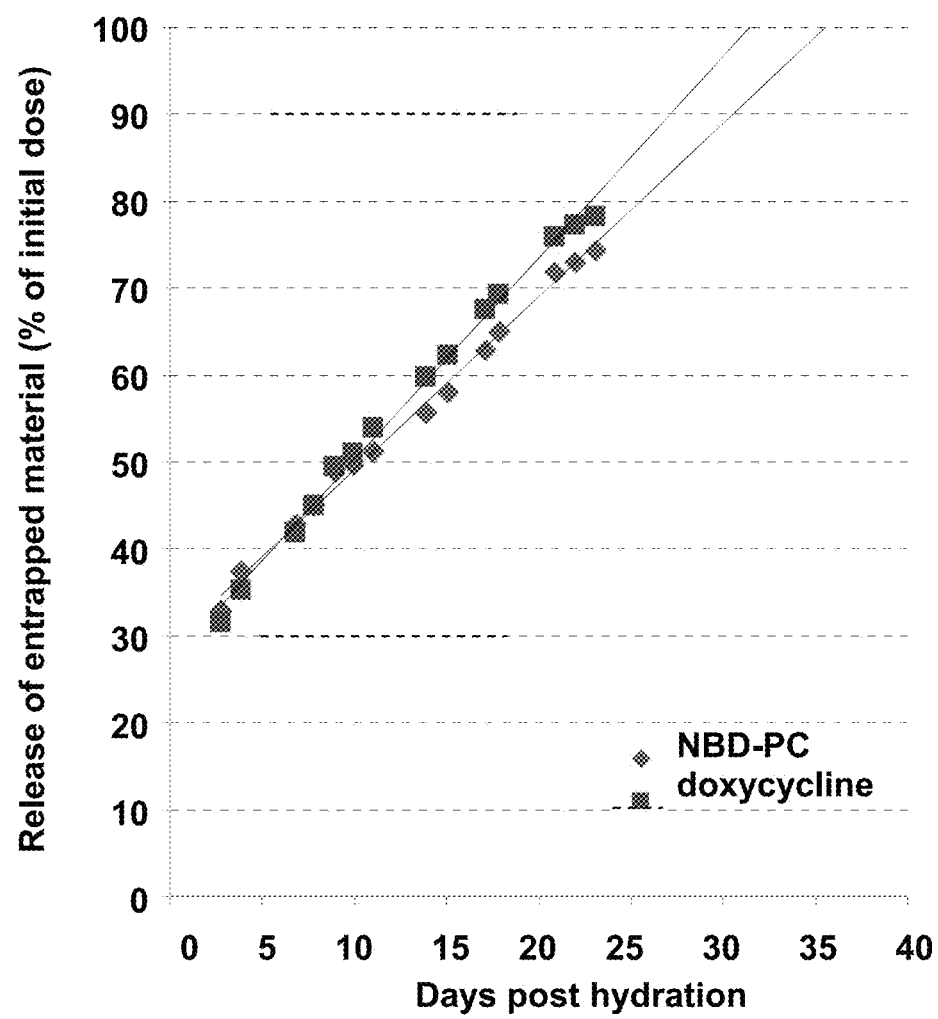
FIG. 15: Encapsulated DOX and fluorescently labeled phosphatidylcholine (NBD-PC) are co-released from the surface of coated bone particles into the surrounding medium (5% FBS at 37° C.) following zero order kinetics.

The described turbidity experiments suggest that the post hydration turbidity seen in the supernatants of hydrated coated bone particles is predominantly controlled by the lipid content of the formulation. The initial high turbidity which is follows by a slower elevation of the turbidity is correlated with the kinetic behavior of DOX release from bone particles coated with the formulation of the invention (FIG. 2) as well as the kinetic behavior of NBD-marked fluorescent phospholipids release (FIG. 15) which is characterized by an initial burst release followed by slow zero order release.

Example 7: Small Angle X-Ray Scattering Analysis of Bone Particles Coated with the Matrix Composition of the Invention We have analyzed the structure of bone particles (TCP artificial bone substitute—commercial) coated with a matrix composition comprising the biopolymer PLGA 85:15, the lipid—DPPC 16:0 and the antibiotic drug—doxycycline hyclate—DOX. The dried particles were loaded into a glass capillary and analyzed by Small Angle X-ray scattering.

Figure 16:
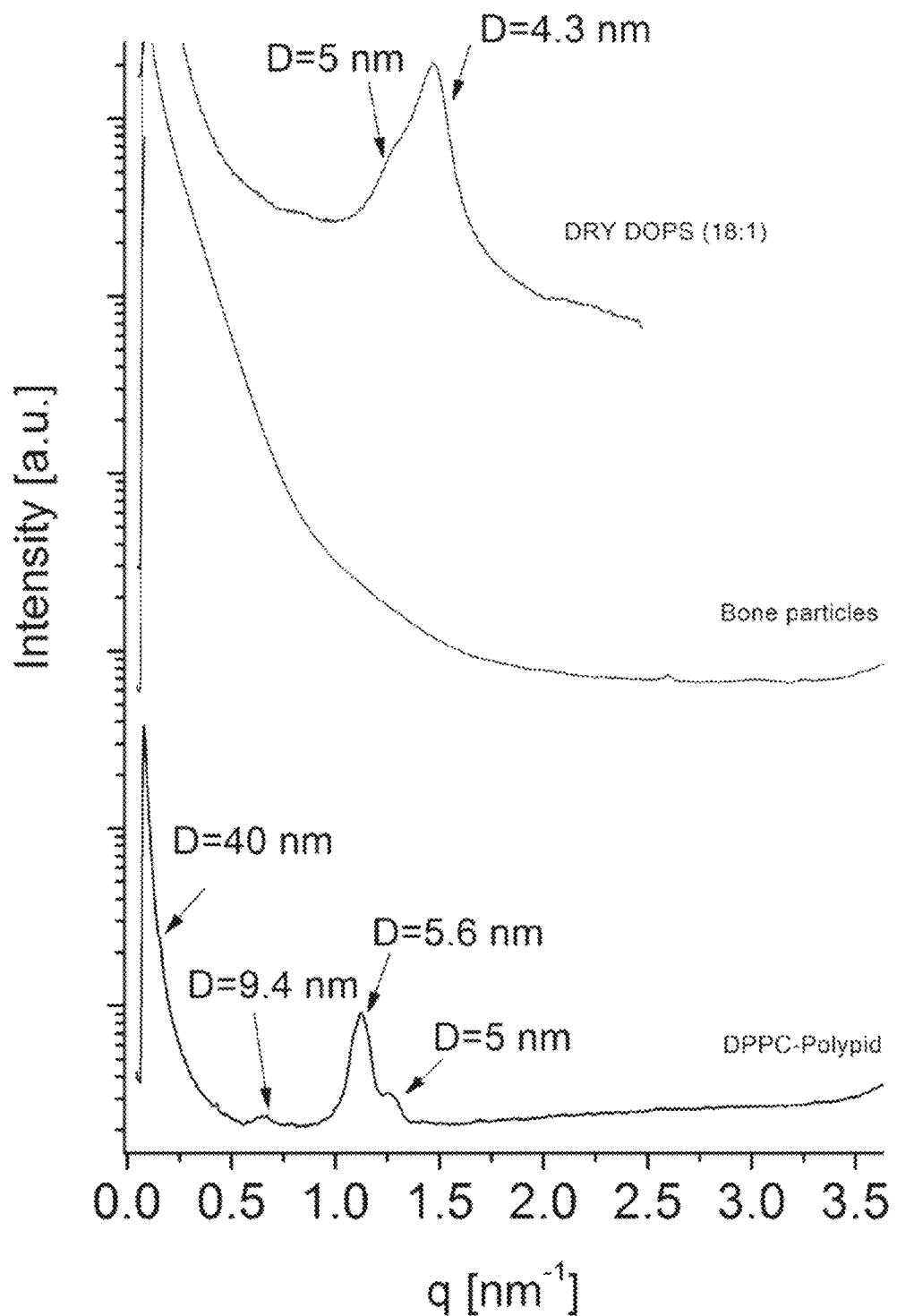
FIG. 16: Small Angle X-ray Scattering (SAXS) analysis of bone particles coated with the matrix formulation of the invention (PLGA 85:15, DPPC 16:0, DOX) reveals the matrix has an ordered structure. As controls, the scattering profile of dried DOPS (18:1) powder and plain, non-coated bone particles were recorded.

Results: The scattering profile of bone particles coated with the matrix formulation as described above, suggest that the matrix formulation has an ordered structure with several sub structures of various sizes ranging from 5 nm to 40 nm (FIG. 16). The structure of a dried phospholipids powder was further analyzed and was found to have an ordered structure having sub-structures smaller than 5 nm. As a control, the structure of plain, uncoated, TCP particles was studied and it was found that it is not characterized by the presence of sub structures of less than 1 nm. Thus, the sub structures observed in the scattering profile of coated bone particles can be attributed to the coating material itself and not to the plain uncoated bone particles.

Figure 17A:
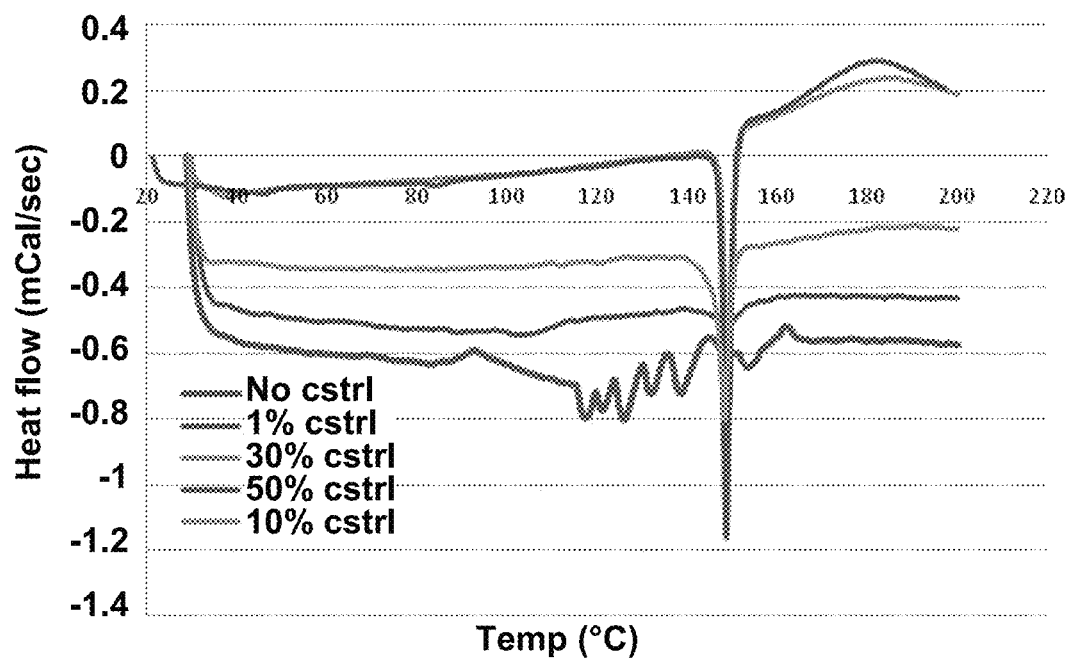
FIGS. 17A and 17B: A. Differential scanning calorimetric analysis (DSC) suggests cholesterol decreases the heat intake by PLGA upon heating. B. PLGA heat uptake decrease was evident in the presence of other lipids such as the antioxidant α-tocopherol, but not with lipids such as mineral oil (containing alkanes with carbon chain of C12-C18).
Figure 17B:
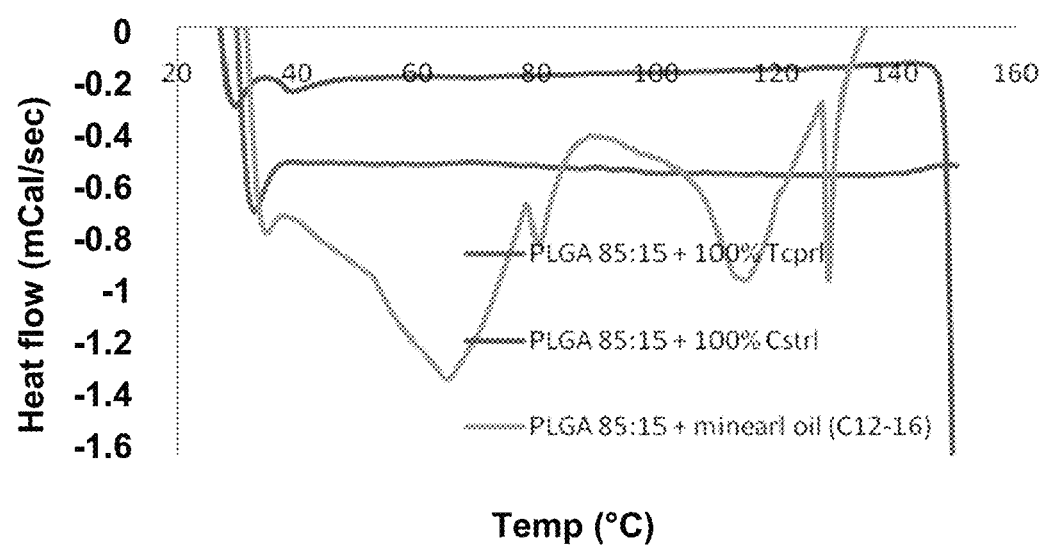

Example 8: Differential Scanning Calorimetric Analysis (DSC) of Polymer Containing Solution (Solution A) with or without Cholesterol Vacuum dried polymer (PLGA (75:25)) was analyzed by differential scanning calorimeter. The temperature of the polymer was raised at a rate of 5° C./min with or without cholesterol (Cstrl) in a different Polymer/cholesterol mass ratio (w/w). A typical calorimetric reaction of PLGA (with no Cstrl) displays an intake of heat during heating up to 200° C. due to PLGA melting. In contrast, the addition of cholesterol decreases the heat uptake by the polymer in a dose response manner, up to the level where almost no heat uptake is evidenced. The narrow heat uptake at about 150° C. is typical the free cholesterol in this system (FIG. 17A). The effect of cholesterol was not affected by the rate of heating (data not shown). Similar but lower effect was evidenced when other lipids such as Alfa tocopherol were introduced to the polymer. In contrast, the heat uptake by the polymer upon heating was unaffected by the presence of fatty acids such as mineral oil (carbonic chain C12-C18). (FIG. 17B)

Example 9

Figure 18A:
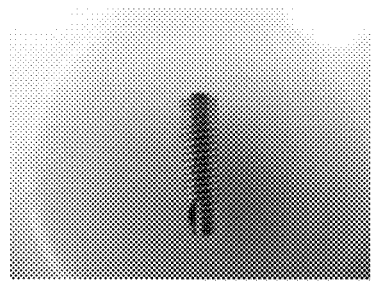
FIGS. 18A and 18B: A dental metal implant made of titanium coated with a matrix formulation comprising PLGA (18:15), DSPC (18:0) cholesterol 10% and 10% DOX. A. The uncoated dental implant. B. the coated implant. The bright color of the coated implant under UV light is due to the fluorescence emission of DOX.
Figure 18B:
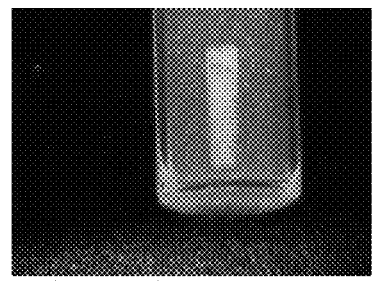

Coating metal implants by the matrix formulations of the invention. Dental implant made of titanium was coated by a matrix formulation (PLGA 85:15, DSPC 18:0, cholesterol 10% and DOX 10%) by immersing the metal in the final solution containing the matrix composition. (see step III example 1) The solvent was than evaporated in an incubator at 37° C., followed by continuous drying under vaccum over night (FIG. 18)

Example 10. Pre-Clinical Testing of Matrix Composition of the Present Invention for Bone Recovery Animal Models:
A. Tibial osteomyelitis in Rabbit
B. Bacteria: *Staphylococcus aureus*

All preclinical testing is performed in accordance with the guidelines for Regulation of Animal Experiments in the State of Israel and according to the Ethics Committee of the research institution.

Test A): Determine the relevant bacterial load for the model:
1. Cause a trauma to the bone (as determined in test A)—10 animals.
2. Fill the void (injured bone) by tricalcium phosphate (TCP) material and seal it with Bone-Wax.
3. Load the site with defined amount of bacteria by injecting it into the site.
4. Duration—~22 days. Clinical signs and body weight (3× weekly) is monitored.
5. At the end of the incubation time: bleed the animal for basic Hematology & Biochemistry blood (prior to the termination of the test).
6. X-Ray of the tibia prior to the termination of the test (day ~20)
7. terminate the experiment, and harvest the tibia for bacteriological test.
8. extract the bacteria from the bone and determine the bacterial concentration (as described below)

Determination of Bacterial Concentration in the Bone Marrow:

The bone marrow and the intramedullary canal is swabbed with sterile cotton tip applicators for gross culture analysis of quality assurance. The inoculated applicator is streaked onto blood plates and then placed into 5 mL of sterile TSB. The plates and tubes are then incubated at 37° C. for 24 h and growth is recorded.

Determination of Bacterial Concentration in the Per Gram of Bone:

The bone is placed into a sterile, 50 mL centrifuge tube and weighed. The bone is then crushed and the final product weighed. Normal sterile saline, 0.90/0, is added in a 3:1 ratio (3 mL saline/g of bone), and the suspensions are vortexed for 2 min. Six 10-fold dilutions of each suspension are prepared with sterile, normal saline, 0.9%. Samples (20 μL) of each dilution, including the initial suspension, are plated, in triplicate, onto blood agar plates and incubated at 37° C. for 24 h; colony forming units are counted at the greatest dilution for each tibia sample. The *S. aureus* concentration is calculated in CFU/g of bone.

Test A) Determine the relevant bacterial load for the model:

| Group | Trauma | Addition of Bacteria | No of animals | Treatment | Duration |
|---|---|---|---|---|---|
| A | Test | Positive | Yes (L) | 3 | TCP (control) 22 days |
| B | Test | Positive | Yes (M) | 3 | TCP (control) 22 days |
| C | Test | Positive | Yes (H) | 3 | TCP (control) 22 days |
| D | Control | Negative | No | 1 | TCP (control) 22 days |

Test B) Determine the Bactericidal Activity of the Matrix Composition of the Invention:
1. Cause a trauma to the bone (as described in test A)—13 animals
2. Fill the void (injured bone) by TCP material and seal it with Bone-Wax.
3. Loading the site with defined amount of bacteria by injecting it into the site (the load will be determine following the result of test A).
4. Duration—~22 days. Clinical signs and body weight (3× weekly) is monitored.
5. During the incubation time: bleed the animals for basic Hematology & Biochemistry blood panel at day 7 and 16 (prior to the termination of the test).
6. X-Ray of the tibia at day 1 (or 2)+at day~20 prior to the termination of the test.
7. Terminate the experiment, and to harvest the tibia for bacteriological tests.
8. Extracting the bacteria from the bone and determining the bacterial concentration: as described above for test A.
9. Local drug concentration is assayed.

Test B) Determine the bactericidal activity of the matrix composition of the invention (BonyPid):

| Group | Trauma | Addition of Bacteria | No of animals | Treatment | Duration |
|---|---|---|---|---|---|
| A | Test | Positive | Yes | 6 | BonyPid | 22 days |
| B | Test | Positive | Yes | 6 | TCP (control) | 22 days |
| C | Control | Positive | no | 1 | TCP (control) | 22 days |

Test C) Toxicology of the Matrix Composition of the Invention:
1. Cause a trauma to the bone (as described in test A)—24 animals
2. Fill the void (injured bone) by TCP material and seal it with Bone-Wax.
3. Loading the site with defined amount of bacteria by injecting it into the site (the load will be determine following the result of test A).
4. Duration—~45 days. Clinical signs and body weight (3× weekly) are monitored. Termination time is determined according to the X-Ray results taken during the incubation time.
5. During the incubation time: bleed the animals for basic Hematology & Biochemistry blood panel at day 0, 10, 30 and 45 (prior to the termination of the test).
6. The animals will be bleeding for blood-drug-concentration analysis at days 1, 3, 10, 16 and 30.
7. X-Ray of the tibia at day 2, 20, 30 and 43 prior to the termination of the test.
8. Terminate the experiment and harvest the tibia for Histology tests.
9. Histology tests for the injured site to 50% of the animals (12 animals).
10. Extracting the bacteria from the bone and determining the bacterial concentration for 50% of the animals (12 animals) as described above.

Test C) Toxicology of the matrix composition of the invention (BonyPid):

| Group | Trauma | Addition of Bacteria | No of animals | Treatment | Duration |
|---|---|---|---|---|---|
| A | Test | Positive | Yes | 6 | BonyPid | 45 days |
| C | Test | Positive | Yes | 6 | BonyPid | 45 days |
| D | Control | Positive | no | 6 | BonyPid | 45 days |
| F | Control | Positive | no | 6 | BonyPid | 45 days |

Example 12. Pre-Clinical Testing in a Periodontitis Animal Model

In a three-stage study, experimental periodontitis in induced in pigs using a cotton ligature placed in a submarginal position. The periodontitis is treated by a combination of scaling and root planing (SRP) and the one of the following treatments:

- Local application of a matrix implant containing very high, high, medium, or low doses (30, 15, 5, and 1 mg/application site, respectively; represented as VH, H, M, and L, respectively) of flurbiprofen and doxycycline.
- Local application of a matrix implant containing no active ingredient, at amounts of matrix corresponding to the amounts of matrix included with the high, medium, and low doses described above (negative control).
- Local application of flurbiprofen and doxycycline, at doses corresponding to the very high, high, medium, and low doses described above, administered as free drug.
- Systemic twice-daily administration of flurbiprofen and doxycycline, at doses corresponding to the high, medium, and low doses described above. This (in combination with SRP) is considered the reference standard for treatment of periodontitis in this animal model.
- No treatment (additional negative control group).

The following parameters are measured daily in each group:

- Carrier marker levels, in order to determine in vivo stability of the carrier in the tissue.
- Levels of flurbiprofen, doxycycline, and their known metabolites in the site of application, the surrounding tissue, and the circulation.
- Toxicity tests.

In addition, the following indicia of efficacy are determined:

- Improvement in clinical parameters such as probing depth (PD), clinical attachment level (CAL), and bleeding on probing (BOP).
- Improvement in radiological parameters such as the distance between the cemento-enamel junction and the alveolar bone crest.
- Histologic analysis.

The number of pigs in each group, study length, and groups in each stage of the study are set forth in Tables 1-3 below:

| STAGE 1 | | | |
|---|---|---|---|
| Experimental groups | Dose | Number | Days |
| Control | — | 2 | 42 |
| Free drugs | VH | 2 | 42 |
| Free drugs | H | 2 | 42 |
| Matrix—no drug | VH | 2 | 42 |
| Matrix—no drug | H | 2 | 42 |
| Matrix with drug | VH | 2 | 42 |
| Matrix with drug | H | 2 | 42 |

| STAGE 2 | | | |
|---|---|---|---|
| Experimental groups | Dose | Number | Days |
| Control | — | 2 | 42 |
| Free drugs | M | 2 | 42 |
| Free drugs | L | 2 | 42 |
| Matrix—no drug | M | 2 | 42 |
| Matrix—no drug | L | 2 | 42 |
| Matrix with drug | M | 2 | 42 |
| Matrix with drug | L | 2 | 42 |

| STAGE 3 | | | |
|---|---|---|---|
| Experimental groups | Dose | Number | Days |
| Control | — | 2 | 56 |
| Reference standard | H | 3 | 56 |
| Reference standard | M | 3 | 56 |
| Reference standard | L | 3 | 56 |
| Free drugs | H | 3 | 56 |
| Free drugs | M | 3 | 56 |
| Free drugs | L | 3 | 56 |
| Matrix—no drug | H | 3 | 56 |
| Matrix—no drug | M | 3 | 56 |
| Matrix—no drug | L | 3 | 56 |
| Matrix with drug | H | 3 | 56 |
| Matrix with drug | M | 3 | 56 |
| Matrix with drug | L | 3 | 56 |

Example 13. Clinical Testing of Matrix Compositions of the Present Invention for Periodontitis The following study tests the safety and clinical, radiological, and microbiologic effects of matrix compositions of the present invention when used as an adjunct to scaling and root planing (SRP).

Scaling and root planing is the most common and conservative form of treatment for periodontal (gum) disease. Scaling is the removal of calculus and plaque that attach to the tooth surfaces. The process especially targets the area below the gum line, along the root. Plaque is more likely to stick to rough surfaces. For this reason, the root surface is smoothed down in a process called root planing. Root planing removes any remaining calculus and smoothes irregular areas of the root surface Study design is longitudinal, randomized, single-masked, and inter-subject. Male and female subjects, aged 20-65 with moderate to severe chronic periodontitis or aggressive periodontitis, are recruited. Detailed medical and dental histories are obtained. Exclusion criteria: 1) a complicating systemic condition, i.e. pregnancy or diabetes; 2) use of systemic antibiotic or NSAID drugs in the past 3 months; 3) smoking; 4) any known allergy to ingredients of the matrix composition; 5) periodontal treatment undertaken less than 6 months prior to baseline. Subjects undergo SRP either alone or in combination with administration of (a) matrix implants containing antibiotic+NSAID drugs; (b) matrix implants containing no active ingredient; (c) orally administered free antibiotic+NSAID drugs; or (d) systemic antibiotic+NSAID drugs. Implants or free antibiotics are administered at multiple sites in the oral cavity.

The following clinical measurements are recorded at baseline, and at 1, 3, 6, and 9 months: probing depth (PD), clinical attachment level (CAL), bleeding on probing (BOP), and gingivitis, plaque, and staining indices.

Microbiological tests, including bacterial culturing and N-benzoyl-DL-arginine-napthylamide (BANA) tests, are performed.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. Tricalcium phosphate (TCP) particles having their surface coated fully or partially with a biocompatible matrix composition, the matrix composition comprising:
   a. a biodegradable polymer;
   b. a first lipid comprising a sterol;
   c. a second lipid comprising at least one phospholipid having hydrocarbon chains of at least 14 carbons; and
   d. a pharmaceutical active agent;
   wherein the matrix composition: (i) is lipid saturated, (ii) has a multilayered structural in which the biodegradable polymer and lipids are ordered in the form of layers and (iii) when maintained in an aqueous environment provides sustained release of the pharmaceutical active agent.

2. The coated particles of claim 1, wherein said phospholipid is a phosphatidylcholine having fatty acid moieties having at least 14 carbons.

3. The coated particles of claim 1 wherein the biodegradable polymer is a biodegradable polyester selected from the group consisting of PLA (polylactic acid), PGA (poly glycolic acid) and PLGA (Poly (lactic co glycolic acid).

4. The coated particles of claim 1 wherein the pharmaceutical active agent is selected from an antibiotic, an antifungal, a non-steroidal anti-inflammatory drug, a steroid, an anti-cancer agent, an osteogenic factor and a bone resorption inhibitor.

5. The coated particles of claim 4, wherein said pharmaceutical active agent is an antibiotic or antifungal.

6. The coated particles of claim 5, wherein the antibiotic is selected from the group consisting of doxycycline and doxycycline hyclate.

7. The coated particles of claim 4, wherein said pharmaceutical active agent is an anticancer agent.

8. The coated particles of claim 7, wherein the anticancer agent is docetaxel.

9. The coated particles of claim 4, wherein said pharmaceutical active agent is a non-steroidal anti-inflammatory drug (NSAID).

10. The coated particles of claim 4, wherein said pharmaceutical active agent is a steroid.

11. The coated particles of claim 10, wherein said steroid is dexamethasone or dexamethasone 21-phosphate.

12. The coated particles of claim 4, wherein said pharmaceutical active agent is selected from an osteogenic factor or a bone resorption inhibitor.

13. The coated particles of claim 1, wherein the weight ratio of total lipids to said biodegradable polymer is between 1.5:1 and 9:1 inclusive.

14. The coated particles of claim 1, comprising a plurality of pharmaceutical active agents selected from an antibiotic, an antifungal, a non-steroidal anti-inflammatory drug (NSAID), a steroid, an anti-cancer agent, an osteogenic factor and a bone resorption inhibitor.

15. The coated particles of claim 1, wherein said matrix composition is homogeneous.

16. The coated particles of claim 1, wherein the matrix composition further comprises an additional lipid selected from the group consisting of: a sphingolipid, a tocopherol, an additional phospholipid selected from the group consisting of a phosphatidylserine, a phosphatidylglycerol, and a phosphatidylinositol, a free fatty acid having 14 or more carbon atoms, a PEGylated lipid and any combination thereof.

17. The coated particles of claim 1, wherein the matrix composition further comprises a targeting moiety capable of interacting with a target molecule selected from the group consisting of a collagen molecule, a fibrin molecule and a heparin.

18. The coated particles of claim 1, wherein said sterol is a cholesterol.

19. The coated particles of claim 18, wherein said cholesterol is present in an amount of 10-50 percent of the total weight of the lipid content of said matrix composition.

20. The coated particles of claim 1, wherein the at least one phospholipid is selected from the group consisting of 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC) and any combination thereof.

21. A pharmaceutical composition comprising the coated particles of claim 1, for sustained release of the pharmaceutically active agent.

* * * * *